US011129657B2

(12) United States Patent
Geist et al.

(10) Patent No.: US 11,129,657 B2
(45) Date of Patent: Sep. 28, 2021

(54) ADJUSTABLE BONE FIXATION SYSTEMS

(71) Applicants: Wyatt Drake Geist, David, FL (US); John Souza, Sr., Monroe, NC (US); Ryan Lewis, Waxhaw, NC (US); Aubrey Clint Folsom, Pelham, AL (US); Marc Von Amsberg, Waxhaw, NC (US)

(72) Inventors: Wyatt Drake Geist, David, FL (US); John Souza, Sr., Monroe, NC (US); Ryan Lewis, Waxhaw, NC (US); Aubrey Clint Folsom, Pelham, AL (US); Marc Von Amsberg, Waxhaw, NC (US)

(73) Assignees: Wyatt Drake Geist, David, FL (US); John Souza, Sr., Monroe, NC (US); Ryan Lewis, Waxhaw, NC (US); Aubrey Clint Folsom, Pelham, AL (US); Marc Von Amsberg, Waxhaw, NC (US)

( * ) Notice: Subject to any disclaimer, the term of this patent is extended or adjusted under 35 U.S.C. 154(b) by 0 days.

(21) Appl. No.: 16/283,384

(22) Filed: Feb. 22, 2019

(65) Prior Publication Data
US 2020/0146725 A1 May 14, 2020

Related U.S. Application Data

(63) Continuation-in-part of application No. PCT/US2017/048480, filed on Aug. 24, 2017.
(Continued)

(51) Int. Cl.
*A61B 17/86* (2006.01)
*A61B 17/70* (2006.01)
*A61B 17/56* (2006.01)

(52) U.S. Cl.
CPC ...... *A61B 17/8685* (2013.01); *A61B 17/7002* (2013.01); *A61B 17/7032* (2013.01);
(Continued)

(58) Field of Classification Search
CPC ............ A61B 17/8685; A61B 17/8625; A61B 17/8605; A61B 17/7035; A61B 17/7037
See application file for complete search history.

(56) References Cited

U.S. PATENT DOCUMENTS 5,209,753 A 5/1993 Biedermann et al.
6,086,589 A 7/2000 Kuslich et al.
(Continued)

FOREIGN PATENT DOCUMENTS

EP 0841876 B1 7/2002
EP 1545355 B1 10/2008
(Continued)

OTHER PUBLICATIONS

Partial Supplementary European Search Report issued for Application No. / Patent No. 17844441.0-132 / 3503827 PCT/US2017/048480 dated Mar. 30, 2020.
(Continued)

*Primary Examiner* — Julianna N Harvey
(74) *Attorney, Agent, or Firm* — McNees Wallace & Nurick LLC

(57) ABSTRACT

The invention is directed in various aspects to a system including anchors, anchor components, and anchor assemblies and subassemblies that are adapted for attachment to a bony structure of a clinical subject. For example, two or more such anchors in the form of screws may be affixed to bones, for example, vertebral structures such as the pedicle, and each anchor is connected to a stabilizer such as a surgical rod that is inserted between the anchors. The anchors and assemblies are novel in many respects owing to
(Continued)

their modular nature, which in contrast to conventional systems, allows the anchors to be provided to a surgeon in modular, subassembly and fully assembled form to enable a broad array of choices in devising the optimal plane for surgical bone fixation.

16 Claims, 17 Drawing Sheets

Related U.S. Application Data

(60) Provisional application No. 62/379,111, filed on Aug. 24, 2016.

(52) U.S. Cl.
CPC ...... *A61B 17/7035* (2013.01); *A61B 17/7037* (2013.01); *A61B 17/7082* (2013.01); *A61B 17/863* (2013.01); *A61B 17/8625* (2013.01); *A61B 17/8695* (2013.01); *A61B 2017/564* (2013.01); *A61B 2017/8655* (2013.01)

(56) References Cited

U.S. PATENT DOCUMENTS

| | | | |
|---|---|---|---|
| 6,626,911 B1 | 9/2003 | Engman et al. | |
| 6,778,861 B1 | 8/2004 | Liebrecht et al. | |
| 7,186,255 B2 | 3/2007 | Baynham et al. | |
| 7,306,603 B2 | 12/2007 | Boehm, Jr. et al. | |
| 7,468,064 B2 | 12/2008 | Bruneau et al. | |
| 7,588,593 B2 | 9/2009 | Aferzon | |
| 7,875,065 B2 | 1/2011 | Jackson | |
| 7,892,257 B2 | 2/2011 | Abdelgany | |
| 7,967,850 B2 | 6/2011 | Jackson | |
| 7,988,694 B2 | 8/2011 | Barrus et al. | |
| 8,052,720 B2 | 11/2011 | Kuester et al. | |
| 8,092,494 B2 | 1/2012 | Butler et al. | |
| 8,162,991 B2 | 4/2012 | Strauss et al. | |
| 8,202,304 B2 | 6/2012 | Boehm, Jr. et al. | |
| 8,361,122 B2 | 1/2013 | Barrus et al. | |
| 8,377,101 B2 | 2/2013 | Barrus et al. | |
| 8,382,802 B2 | 2/2013 | Boehm, Jr. et al. | |
| 8,623,061 B2 | 1/2014 | Quevedo et al. | |
| 8,790,374 B2 | 7/2014 | Lott et al. | |
| 8,852,239 B2 | 10/2014 | Jackson et al. | |
| 10,117,679 B2 | 11/2018 | Biyani et al. | |
| 2004/0147929 A1 | 7/2004 | Biedermann et al. | |
| 2005/0055026 A1 | 3/2005 | Biedermann et al. | |
| 2005/0273101 A1* | 12/2005 | Schumacher | A61B 17/7037 606/306 |
| 2006/0241593 A1 | 10/2006 | Sherman et al. | |
| 2007/0233062 A1 | 10/2007 | Berry | |
| 2007/0270855 A1 | 11/2007 | Partin | |
| 2008/0147129 A1 | 6/2008 | Biedermann et al. | |
| 2008/0161863 A1 | 7/2008 | Arnold et al. | |
| 2008/0312701 A1 | 12/2008 | Butters et al. | |
| 2009/0036929 A1 | 2/2009 | Reglos et al. | |
| 2009/0062868 A1 | 3/2009 | Casutt | |
| 2009/0105771 A1* | 4/2009 | Lei | A61B 17/7037 606/313 |
| 2009/0157123 A1 | 6/2009 | Appenzeller et al. | |
| 2010/0114108 A1 | 5/2010 | Strauss | |
| 2010/0249846 A1 | 9/2010 | Simonson | |
| 2011/0230915 A1 | 9/2011 | Anderson et al. | |
| 2011/0307013 A1 | 12/2011 | Winslow et al. | |
| 2011/0319946 A1 | 12/2011 | Levy et al. | |
| 2012/0016423 A1 | 1/2012 | Hua | |
| 2012/0041490 A1 | 2/2012 | Jacob et al. | |
| 2012/0203288 A1 | 8/2012 | Lange et al. | |
| 2012/0215264 A1* | 8/2012 | Lee | A61B 17/8685 606/305 |
| 2012/0271353 A1 | 10/2012 | Barry | |
| 2012/0316609 A1 | 12/2012 | Wall et al. | |
| 2013/0144342 A1 | 6/2013 | Strauss et al. | |
| 2013/0172937 A1 | 7/2013 | Davenport et al. | |
| 2014/0094860 A1 | 4/2014 | Reimels | |
| 2014/0277187 A1 | 9/2014 | Fang et al. | |
| 2014/0288605 A1 | 9/2014 | Mesiwala et al. | |
| 2014/0336709 A1 | 11/2014 | Avidano et al. | |
| 2014/0358182 A1 | 12/2014 | Puekert | |
| 2015/0100093 A1 | 4/2015 | Harper | |
| 2016/0270826 A1 | 9/2016 | Marino et al. | |
| 2016/0331421 A1* | 11/2016 | Little | A61B 17/863 |
| 2017/0112555 A1 | 4/2017 | Wallenstein et al. | |
| 2019/0125410 A1 | 5/2019 | Harwell | |
| 2019/0133660 A1 | 5/2019 | Lindner | |
| 2019/0159820 A1 | 5/2019 | Geist et al. | |
| 2020/0030006 A1* | 1/2020 | Errico | A61B 17/7035 |

FOREIGN PATENT DOCUMENTS

| | | |
|---|---|---|
| RU | 2189200 C2 | 9/2002 |
| RU | 2003133987 A | 4/2005 |
| WO | 2005044117 A2 | 5/2005 |
| WO | WO2005044117 | 5/2005 |
| WO | WO2016054951 | 7/2008 |
| WO | WO2009079329 | 6/2009 |

OTHER PUBLICATIONS

Non-Final Office Action issued by USPTO for U.S. Appl. No. 16/018,942 dated Aug. 1, 2019.
Final Office Action issued by USPTO for U.S. Appl. No. 16/018,942 dated Jan. 15, 2020.
Notice of Allowance issued by USPTO for U.S. Appl. No. 16/018,942 dated Apr. 22, 2020.
International Search Report and Written Opinion from PCT/US2019/039026 dated Sep. 19, 2019.
Rasoulinejad, Parham, Design and Development of a Novel Expanding Pedicle Screw for Use in the Osteoporotic Lumbar Spine, Western University Graduate & Postdocotoral Studies, Electronic Thesis and Dissertation Repository, 2013, Paper 1614.
International Search Report and Written Opinion from corresponding International Application PCT/US2017/048480.

\* cited by examiner

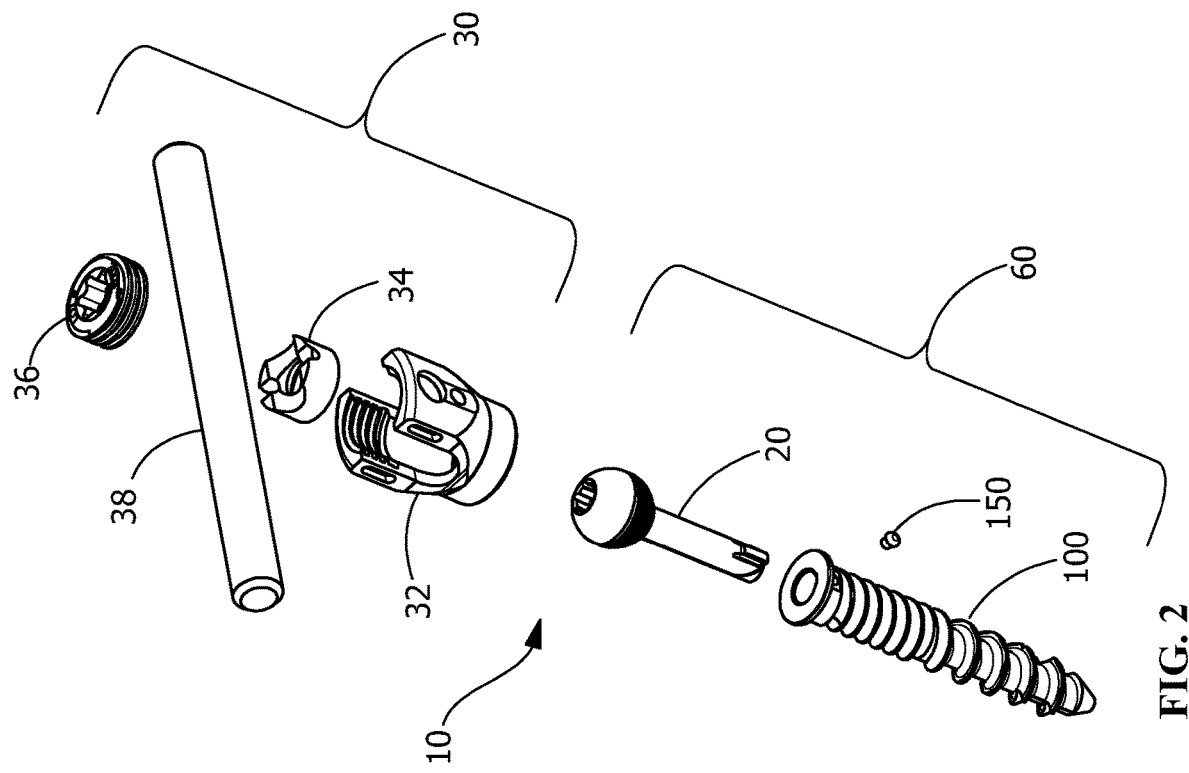
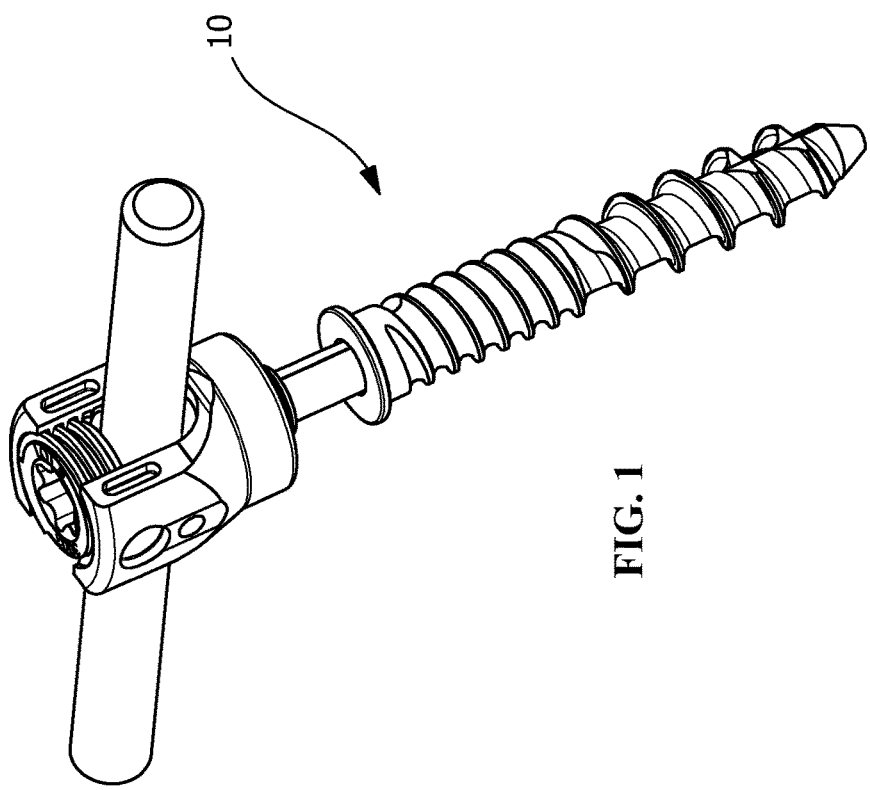

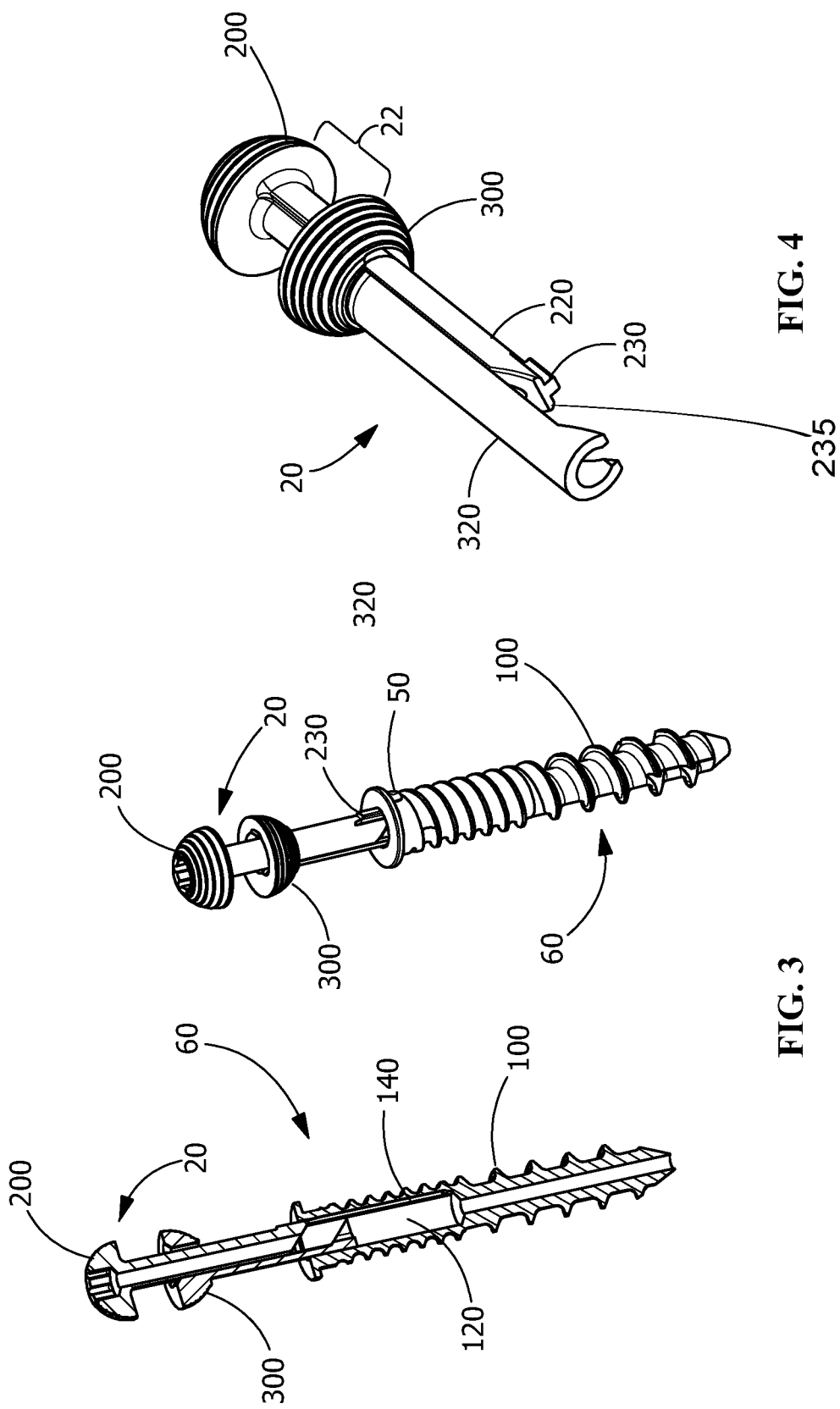

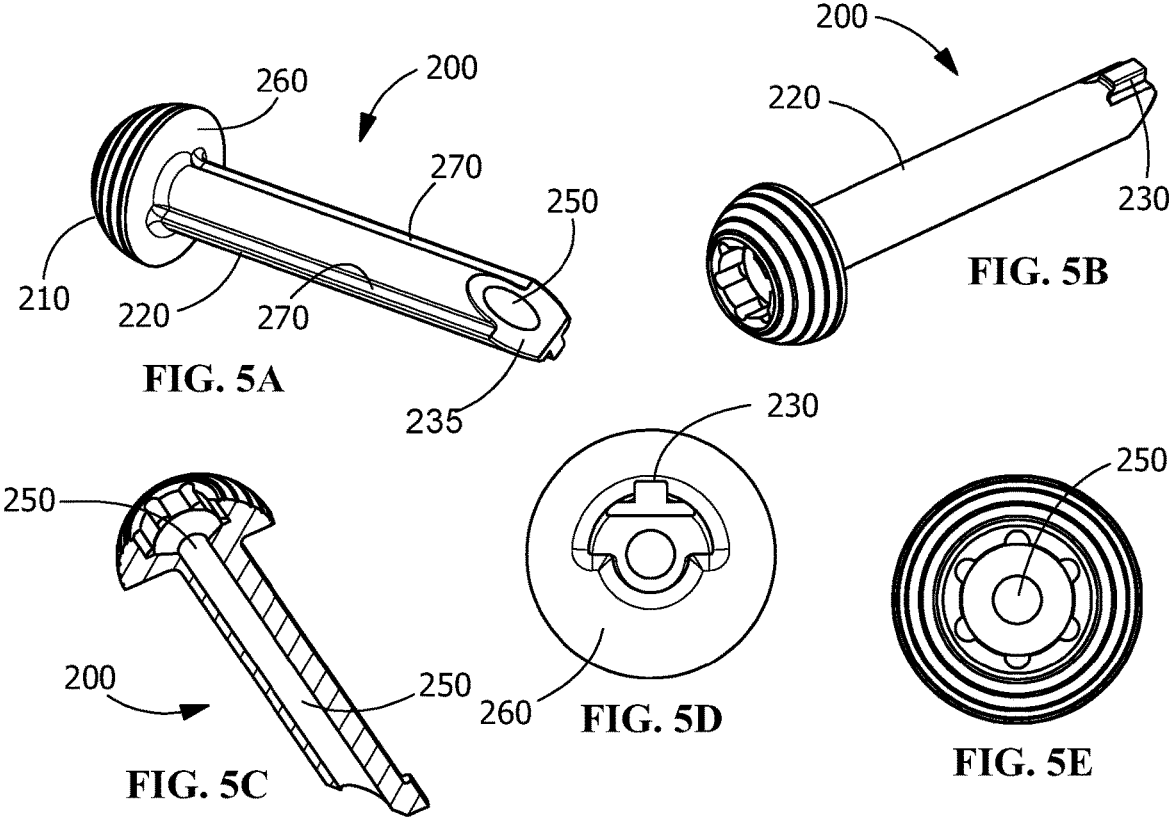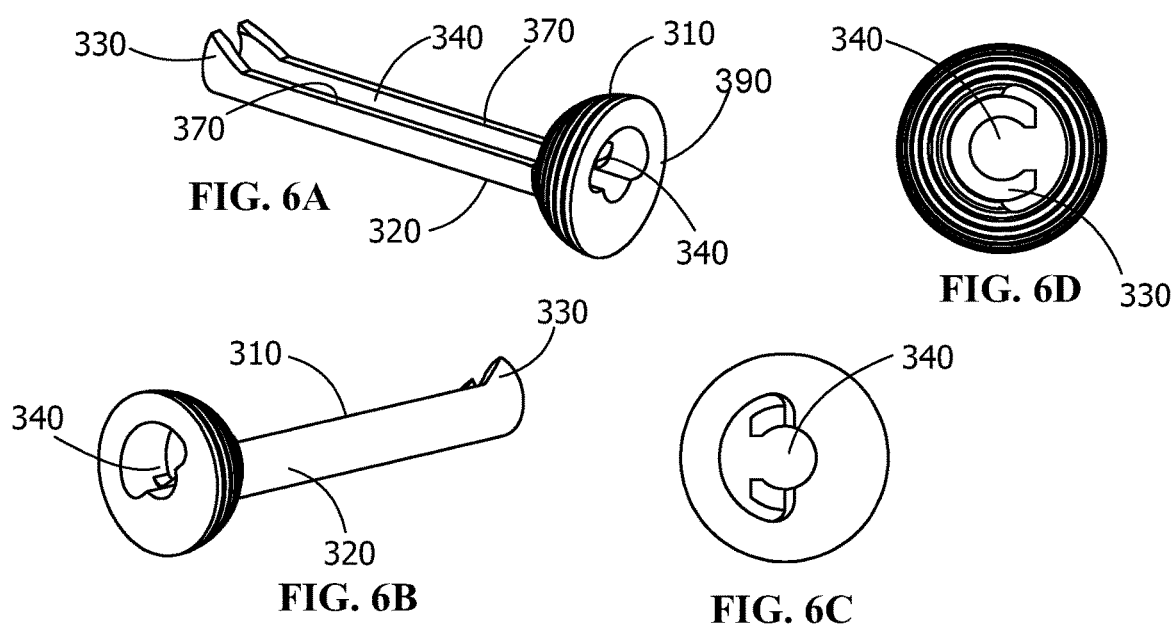

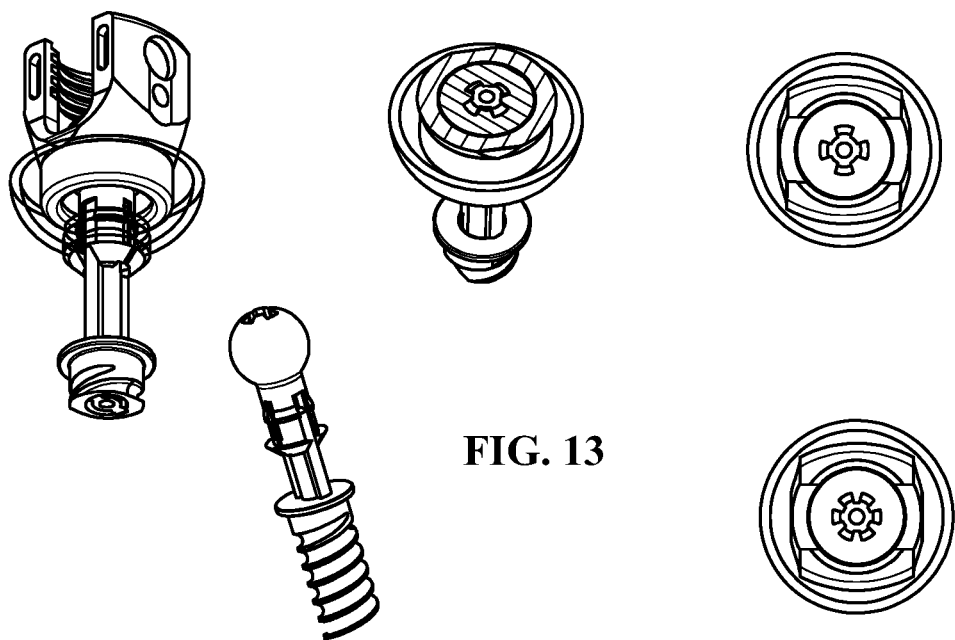
FIG. 13
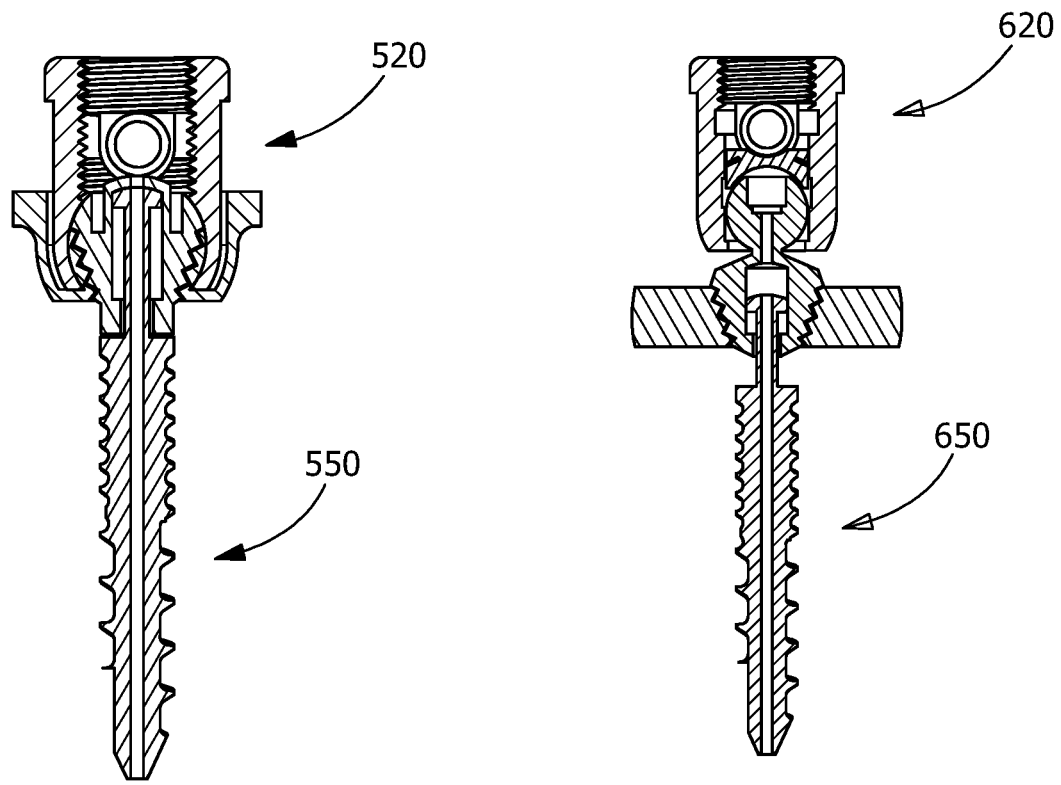
FIG. 14
FIG. 15

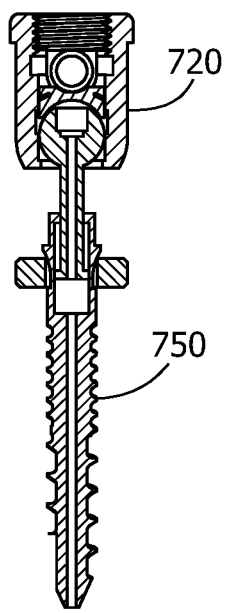
FIG. 16
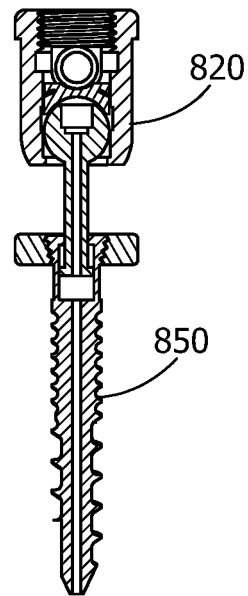
FIG. 17
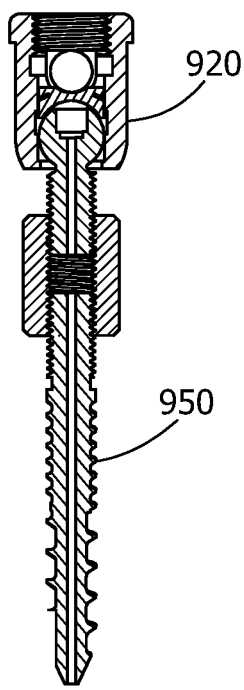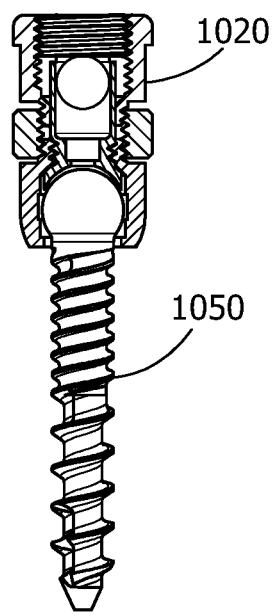
FIG. 18

ADJUSTABLE BONE FIXATION SYSTEMS

PRIORITY

The present application is a continuation-in-part application and claims priority to Patent Cooperation Treaty Patent Application No. PCT/US2017/048480, filed Aug. 24, 2017 which claims priority to and the benefit of U.S. Provisional Patent Application No. 62/379,111, filed Aug. 24, 2016, with the title "ADJUSTABLE BONE FIXATION SYSTEMS," the entireties of which are hereby incorporated by reference herein.

FIELD OF INVENTION

The present invention relates to modular and adjustable assemblies for achieving alignment and fixation of two or more bones or bone segments. In particular embodiments, the invention relates to modular and adjustable assemblies for achieving fixation of bones in the spine.

BACKGROUND

The human skeleton is formed of bones, each bone performing a structural role, either individually or collectively with other bones. For example, the spine, which surrounds and protects the spinal cord and associated nerves, provides structure to the body, and enables fluid movement in many planes. Constructed of essentially twenty-four stacked vertebrae, the spine includes seven cervical vertebrae, twelve thoracic vertebrae and five lumbar vertebrae. A healthy spine is flexible in multiple directions to enable a broad range of physical movement. Intervertebral disks are disposed between adjacent vertebrae and provide cushioning and dampening to protect the spinal column and nerves in response to the various translational and rotational forces associated with body motion. Maintenance of the structural integrity and approximate axial alignment of the vertebrae is one key to good health.

A clinical subject's spine may be damaged or otherwise compromised in one of many ways. Abnormalities of or damage to the spine include but are not limited to scoliosis (abnormal lateral curvature), kyphosis, excessive lordosis, spondylolisthesis, displaced, degenerative or ruptured discs, fractures to one or more vertebral bodies and tumors. These and other possible spinal conditions directly and adversely affect mobility, and also cause moderate to extreme or even debilitating pain, at times accompanied by diminished or lost nerve function.

To ameliorate pain and restore loss of function associated with spinal conditions, a variety of conventional procedures have been developed using an array of mechanical surgical systems and implants that can secure two or more vertebrae in a relatively fixed position and can stabilize and straighten spinal deviations along the spinal axis. A stabilization system can be used without fusion treatment of the spine, or in conjunction with fusion treatment of the spine wherein one or more spacing devices is used to replace all or a portion of a vertebral disc. Typically, such discal implants are used together with natural bone components obtained from the clinical subject or a donor source, artificial bone, other biologic components to promote bone growth and fusion between the adjacent vertebral bodies. One or more such replacements may be accomplished in a spinal fixation surgery. The fixation system, with or without fusion components, operates to create a substantially rigid construct of bone and mechanical hardware that replaces damaged or diseased vertebrae and connects them to relatively healthier adjacent vertebrae.

Generally, spinal fixation systems involve some mode of stabilization using one or more rigid or substantially rigid surgical stabilization elements, such as a rod or a plate, and means for fastening and securing the stabilization element to bone. Fastening means can include one or more bone anchors, such as screws or bolts, assembled with connectors that enable engagement with one or more stabilization elements. The connectors may include hooks, clamps, cross connectors and other structures that engage with one or more of stabilization elements and anchors. These systems of anchor and connector assemblies and stabilization elements are secured to two or more vertebrae and are interconnected to provide support, encourage alignment or realignment of the vertebrae, and to achieve immobilization and fusion.

When spinal fixation surgery is performed from the anterior aspect of the clinical subject, it is conventional practice to affix a stabilization element in the form of a thin plate, typically formed of metal, to adjacent vertebral bodies and secure the plate using anchors, such as screws. When the fixation surgery is performed from the posterior aspect of the clinical subject, it is conventional practice to affix bone anchors into the vertebral bodies, typically in the pedicle. Multiple levels of adjacent vertebrae may be fixed in this manner. Interconnection of the secured anchors to the stabilization element creates a rigid fixation between the adjacent vertebral bodies.

The mode of surgical access may be open, that is, involving a relatively extensive resection of the soft tissue to plainly expose the vertebrae to be fixated. In some examples, the mode of surgical access may be minimal, wherein less invasive surgical techniques are used to minimize tissue resection. These less invasive approaches have many benefits to the clinical subject, however, the associated reduction in direct access and visualization of the vertebral tissue practically means that the anchor implants are difficult to access, grasp and manipulate with instruments, thus complicating the surgeon's efforts and often prolonging the length of time that the clinical subject is in surgery.

Among the many challenges associated with placement of vertebral stabilization systems is the fact that adjacent vertebrae are typically not perfectly aligned. Indeed, along any particular length of a spine, a series of adjacent vertebrae can deviate laterally a great deal from the central axis of the spine. Further, as a result of natural spinal curvature and any vertebral defects, corresponding portions, such as pedicles, of adjacent vertebra are not in the same plane. In the context of implanting spinal fixation systems, these variations can be accommodated to some extent by introducing bends or curves in the substantially rigid stabilization element(s) used for fixation. But in instances where the therapeutic benefit is obtained by realigning adjacent vertebrae, adjustment of the curvature of the stabilization element(s) is not a completely satisfactory solution. Accordingly, it is typically the case that the surgeon and surgical team must manipulate the spine and the system instruments in an attempt to align the secured anchors for attachment to a stabilization element. Often, the extent of nonalignment, both in terms of longitudinal and vertical planar positions of vertebrae along the spine, can cause failure of one or more of the system components, extend surgery, cause damage to the clinical subject's spine, and ultimately lead to a less than desirable clinical outcome. The challenges of access in minimally invasive procedures can compound the difficulties associated with non-aligned vertebral bodies.

Attempts have been made in the design of spinal fixation systems to address variability of spinal anatomy, such as those variations described above. In many examples of conventional systems, anchors are adapted to achieve a range of variability in positioning based on pivotal rotation of the anchor such that the axis of the secured anchor relative to the stabilization element can be varied. These are referred to as poly-axial and uni-axial anchors. They are useful in particular for facilitating attachment of a stabilization element to two or more vertebrae that are not aligned along the spinal axis. There are other examples of systems that are adapted with features that facilitate engagement of non-axially aligned vertebrae. But there are no conventional systems suitable for accommodating the variability in the relative height of adjacent vertebrae, wherein corresponding portions of adjacent vertebrae are not on the same plane. Further, there are no conventional systems that allow the surgeon the option to install bone anchors into the bone and then select from a suite of modular anchor components to achieve an optimized system for fixation that avoids or minimizes the problems associated with anatomical variations in the spine. Beyond the spine, such as for other bones and bone fragments in the body, there are likewise no systems that provide either or both modularity and length adjustability options in the fixation or reduction of bones and bone fragments.

To address the above-described challenges, there is need for bone anchors and other implants that meet or exceed the functionality of conventional anchors while also providing adjustability, and ideally, modularity, to address the height variability of vertebral bodies that do not share a common plane. Thus, what is needed, for example in the context of the spine, is a fixation system that includes one or more anchors that are capable of mono-, uni-, and poly-axial positioning and allow substantial vertical travel between the distal attachment point in the bone and the proximal position of a stabilization element, and are capable of locking to avoid further vertical travel after the system implantation is completed. Such an anchor would enable simplified attachment of adjacent anchors to a stabilization element by reducing the extent of height variability of adjacent anchors, thereby avoiding many of the challenges faced in the surgical setting.

SUMMARY

The present invention describes various exemplary systems, methods and apparatuses for installation of one or more anchors and stabilization elements that are adapted for height adjustability during spinal fixation surgery. The disclosure is directed in various embodiments, both described and contemplated, to assemblies, subassemblies and modular components and their methods of use and installation for achieving adjustable fixation and/or reduction of bones and bone fragments.

Frequent reference is made herein to fixation systems that include anchors in the form of vertebral pedicle screws, and stabilization elements in the form of one or more surgical rods. It will be appreciated by those skilled in the art that the spine is but one example of a bone or bone system that may be the object of surgical correction, and thus, pedicle screws and rods are mere examples of the bone anchor, and vertebral stabilization system components contemplated herein. In other examples, anchors may be screws for engagement with a tether or other tensioning means, or with one or more plates or rods or combinations of these. And anchors and systems described herein may be suitable for other bones and bone systems in the body. Moreover, it will be appreciated that the mechanisms for adjustment of anchor length can be adapted for use with other anchor and fixation and stabilization elements used in orthopedic applications in the spine or in other parts of the body.

In one example, spinal rods may be made adjustable according to the features disclosed herein to enable tuned adjustment of rod length at the time of implantation or subsequently as spinal healing and or adjustment takes place, such as for adjustment of rod length in connection with scoliosis treatment. In yet other examples, adjustable anchors may be employed in the reduction or fixation of other bones, such as bones of the hand, or of the foot or in other locations where adjustment of the length of an anchor or other fixation element is desirable. One such example would be incorporation of adjustability features disclosed herein in dual threaded headless screws or screws, rods or pins with other head and threading configurations that are used for interconnecting and reducing fractured bone fragments or adjacent bones. Such anchors adapted according to the instant disclosure would enable tuned adjustment of implant length to accommodate anatomical variations in a clinical subject and achieve optimized anchor placement.

BRIEF DESCRIPTION OF THE DRAWINGS

Various embodiments of the disclosed inventions will now be discussed with reference to the appended drawings. These drawings merely depict representative embodiments and are not limiting in scope.

FIG. 1 shows a perspective view of a locked assembly according to the disclosure;

FIG. 2 shows and exploded perspective view of the assembly shown in FIG. 1;

FIG. 3 shows in alternate unlocked whole and cutaway views, a subassembly of the assembly shown in FIG. 1;

FIG. 4 shows A subassembly of the assembly shown in FIG. 3;

FIG. 5 (A) shows a perspective view of a first side looking from the distal toward the proximal end;

FIG. 5 (B) shows a perspective view of a second side looking from the proximal to the distal end;

FIG. 5 (C) shows a perspective cutaway view of the top side looking from the top toward the distal end;

FIG. 5 (D) shows a planar view of the top end looking through the cannulation from the proximal to the distal end;

FIG. 5 (E) shows a planar view of the bottom end looking through the cannulation from the distal to the proximal end;

FIG. 6 (A) shows a perspective view of a first side looking from the proximal toward the distal end;

FIG. 6 (B) shows a perspective view of a second side looking from the proximal to the distal end;

FIG. 6 (C) shows a planar view of the top end looking through the cannulation from the proximal to the distal end;

FIG. 6 (D) shows a planar view of the bottom end looking through the cannulation from the distal to the proximal end;

FIG. 13 shows alternate views of the assembly shown in FIG. 12;

FIG. 14 shows an alternate embodiment of the anchor assembly as disclosed herein;

FIG. 15 shows an alternate embodiment of the anchor assembly as disclosed herein;

FIG. 16 shows an alternate embodiment of the anchor assembly as disclosed herein;

FIG. 17 shows an alternate embodiment of the anchor assembly as disclosed herein;

FIG. 18 shows an alternate embodiment of the anchor assembly as disclosed herein;

DETAILED DESCRIPTION

Figure 8:
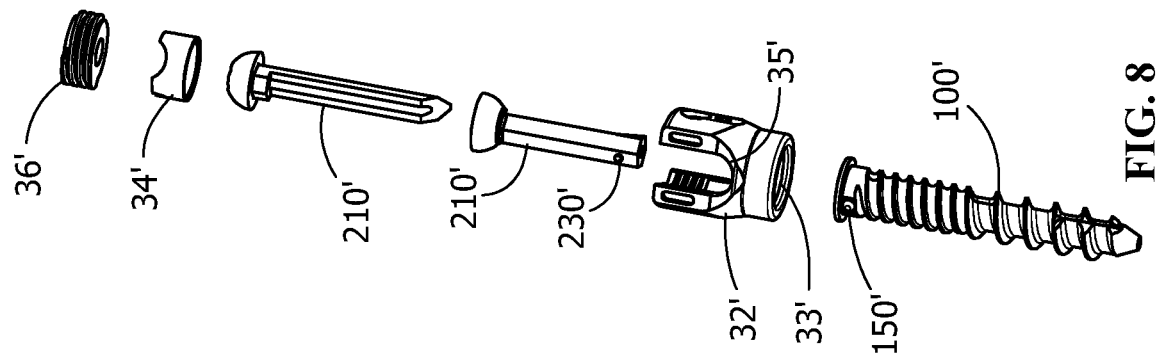
FIG. 8 shows alternate exploded and end views of the anchor assembly components of another embodiment disclosed herein.

This Detailed Description describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The general inventive concepts will now be described with occasional reference to the exemplary embodiments of the invention. This general inventive concept may, however, be embodied in different forms and should not be construed as limited to the embodiments set forth herein. Rather, these embodiments are provided so that this disclosure will be thorough and complete, and will fully convey the scope of the inventive concepts to those skilled in the art.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). A "clinical subject" refers to a human or other animal who is the subject of treatment with a bone fixation or reduction device in accordance with the disclosure. With respect to any references herein that may be made relative to a clinical subject, the term "cephalad" indicates a direction toward the head of the clinical subject, and the term "caudad" indicates a direction toward the feet of the clinical subject. The term "posterior" indicates a direction toward the back of the clinical subject, the term "anterior" indicates a direction toward the front of the clinical subject, and the term "lateral" indicates a direction toward a side of the clinical subject.

The term "height" as used specifically herein pertains to references to the spine of a clinical subject and refers to the relative position of one or both of vertebrae and anchors along adjacent portions or the length of the spine. Likewise, the terms "vertical" and "vertical adjustment" relate to the relative height variations and adjustments thereof with respect to one or both of vertebrae and anchors along adjacent portions or the length of the spine in the context of a clinical subject in a prone position wherein a length adjustment to an anchor would be in a vertical dimension from anterior to posterior. These descriptors are not intended to be limiting with respect to embodiments of the modular adjustable assemblies, subassemblies and components according to the instant invention that are useful outside of the spine, and may more generically be substituted with alternate descriptors including "length" and "length adjustment" where orientation of the clinical subject or body part and bones and implants vary.

As used herein in the described and illustrated embodiments, the term anchor typically refers to the screw component of an anchor assembly or subassembly, and the term anchor assembly refers to the screw component together with attachment features, such as a conventional tulip head or other type of attachment device, and one or more of compression washers and set screws, and optionally additional fixation components. Subassemblies also refer to the modular components of the screw, such as, for example, the shank and head portions and subassemblies of these. More generically, anchor components, subassemblies and assemblies can be adapted to include features suitable for use with any bones in a clinical subject, wherein the modular and adjustable features are as described and claimed herein.

Unless otherwise indicated, all numbers expressing quantities of materials, properties such as length, diameter, and so forth as used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

Bone Anchors, Systems and Methods

The invention is directed in various aspects to a system including assemblies and subassemblies, components including anchors and anchor components adapted for attachment to a bony structure of a clinical subject. In an exemplary embodiment wherein the use is in connection with fixation of the spine, wherein one, two or more such anchors in the form of screws are affixed to bones, for example, vertebral structures such as the pedicle, and each anchor is connected to a stabilizer such as a surgical rod that is inserted between the anchors. The anchors are novel in many respects owing to their modular nature and thus the options to provide the anchors in modular, sub-assembled and assembled forms provide a broad array of choices for the surgeon in devising the optimal surgical fixation plan.

In use by a surgeon, installation of the inventive components of the exemplary bone anchor system for spinal fixation described above includes: selecting two or more bone anchor assemblies or subassemblies, including assemblies and subassemblies selected from pre-assembled and top loading forms, wherein at least one anchor assembly includes an adjustable bone anchor; selecting a stabilization element; using a suitable driver to drive each of two or more anchors or anchor subassemblies into fixed engagement with corresponding vertebrae, wherein at least one anchor or anchor subassembly includes or is adapted to engage with modular components that allow adjustability, including translation along the vertical axis of the anchor, so as to enable selection of the anchor height by the surgeon; engaging a proximal portion of the modular adjustable anchor, such modular portion selected from a pre-assembled or modular screw head and engagement seat, to provide a means to introduce the stabilization element into engagement with the anchor; optionally incrementally adjusting the height of the anchor so as to achieve engagement of the stabilization element in the anchor; sliding the stabilization element into place within the anchor; introducing a fixation element to at least temporarily fix the stabilization element within the anchor; optionally, adjusting at least the vertical position of the anchor to optimize its height orientation relative to the stabilization element and adjacent anchors; tightening the fixation element to compress the stabilization element within the anchor assembly, thereby fixedly engaging the modular components of the anchor so as to lock the position of the anchor and also lock its engagement with the stabilization element. This process is repeated for each adjustable anchor in the system, and conventional methods are used with conventional anchors.

It will be appreciated by one of skill in the art that the modular adjustable anchors described herein may be employed with components of a conventional spinal stabilization system, and may be used on a single vertebra, or traversing two or more vertebra, and may be used in conjunction with fusion or non-fusion treatment of the spine. Of course, in various examples, the anchors may be employed in isolation or in systems that include two or more anchors, connectors and stabilization elements, and the anchors may be deployed other than along the spinal axis. Thus, in other examples of use, two or more anchors may be used to secure one or more stabilization elements that extend either laterally or from an anterior to posterior aspect to traverse a vertebral body, or that wrap around one or more vertebral bodies, or combinations of these. And Of course, it will be appreciated that in some examples the assemblies and subassemblies, components, including anchors and anchor components, may be used in bones of the body other than the spine, and as such may be used individually, as a plurality, or in combination with other devices, and combinations of these.

Referring now to the drawings, an embodiment of an adjustable anchor assembly in accordance with the invention is shown in FIG. 1. The depicted embodiment is representative of generic spinal implants that include a rod, while the specific assembly shown includes a plurality of essentially co-axial components that are novel in their modularity and adjustability. The depicted anchor assembly 10 represents the general components of a pedicle screw implant used for vertebral fixation, and as such, includes: a seat or housing, typically referred to as a tulip head 32, having a bore 33 for receiving a shank of a screw 60 there-through and a receiving seat 35 for engagement with a rod 38; a screw 60 with a threaded shank 100 and a generally spherical screw head 20 that engages with the tulip head 32 housing when the screw 60 is positioned in the bore 33 of the tulip head 32; a compression washer 34 that engages the screw head 20 and is contacted by the rod 38 when the screw 20 and rod 38 are within the tulip head 32 and functions to uniformly translate compressive force to the screw; and a locking nut 36 (for example, as shown in the drawings, a set screw) that engages with the tulip head 32 to secure the rod 38 in its receiving seat 35 and lock the anchor assembly 10 in connection with the rod 38. When assembled and engaged, the anchor assembly 10 components are co-axial, as shown. It will be appreciated that fewer and varied elements of an anchor assembly 10 may be used in accordance with the embodiments of the instant disclosure, including assemblies that are not adapted for use in the spine and are adapted for use in other bones, without departing from the scope of the invention as it is directed to modular anchors and modular anchor assemblies suitable for fixation of a stabilization element to a bone.

In various embodiments, the anchor assembly may be provided for use by a surgeon in a pre-assembled state, completely disassembled, or in some state of subassembly. The depicted assembly for a spinal system is adapted to function as poly-axial, uni-axial or mono-axial according to designs that are conventionally known in the art, and in such various embodiments the assembly selected can allow for axial, and optionally multi-planar adjustment of the anchor. In the various embodiments, screws can be of varying diameter, varying length, and can be cannulated or non-cannulated, fenestrated or non-fenestrated, tapered or non-tapered, self tapping or non-self tapping, and may have any of a variety of types of threading. Moreover, the assembly may be provided in a top- or bottom-loading format, wherein the screw component of the assembly is inserted into the tulip head either from the top or from the bottom, allowing in the instance of bottom loading screws, the ability of the surgeon to implant the shank of the screw and subsequently engage a selected screw head chosen from a selection that may vary in length or other feature, a selected stabilization element chosen from a selection that may vary in instrument attachment features, height or other feature, and combinations thereof. Examples of top- and bottom-loading tulip head configurations are generally known in the art as pre-assembled systems that are not typically adaptable within the surgical suite.

Generally, in accordance with the various embodiments depicted herein, the tulip head is merely representative of conventional designs, and is thus, non-limiting to the extent that its function does not interfere with the operability of the vertically adjustable modular threaded shank portion. In accordance with the depicted embodiment, locking of the assembly with the rod is achieved as with a conventional system, and the locking of the system is independent of the locking of the vertical position. The upper portion of the threaded shank portion terminates in a screw head, which is generally spherical or hemispherical, and includes a feature suitable for engagement of a torque tool to achieve insertion into bone. The driving feature may be selected, for example, from a recess, or an extension, that is complementary to the shape of a tool or driver. An example of a recess feature is a hex head recess that is complementary to a hex head screwdriver. Further, the screw portion of the assembly may have an alternate head shape, such as a hemispherical shape that is spherical for engagement with the tulip head and substantially flat or planer on its upper surface and is engageable with a suitable engaging washer or other feature to allow for direct or indirect compression through the compressive action of a rod inserted and locked in the assembly. Other features of the anchor assembly that may be conventional include features in the threaded shank portion that enable torque driven engagement within bone, which features are present on the terminal head portion of the threaded shank portion and can be actuated independent of the vertically adjustable collet feature of some embodiments described herein. In some embodiments the engagement feature is a recess, such as a hex shaped recess for engagement with a hex driver, and in other possible embodiments the engagement feature is a positive structure that can be gripped by a suitable tool for rotation and torque driven engagement of the threaded distal portion with bone. It will be appreciated by one of skill in the art that the various embodiments described herein and depicted in the drawings are merely representative, and various elements thereof may be varied or interchanged in connection with the features disclosed to achieve the vertical translation contemplated to enable the benefits as described herein.

The assemblies, subassemblies and components described herein can be formed from any one or more suitable biocompatible material and combinations thereof, including those used conventionally in the orthopedics art. Such materials include but are not limited to: metals such as, for example, stainless steel, titanium alloys, cobalt alloys, superelastic metals, such as nitinol; polymers, such as polyester and polyethylene, polyether ether ketone (PEEK); and resorbable synthetic materials such as, for example, suture material and polylactic acid.

Modular Adjustable Assemblies and Components

In various embodiments, as shown in the figures described herein below, the anchor assemblies include modular components that are not present in conventional anchors and that engage to enable implantation and adjustability by means of adjustable modular anchor components. In some embodiments as described herein below such adjustability is along the long axis of the screw to achieve varying heights. Generally, according to the invention, the anchor assemblies have features in common wherein the vertical position of the anchor is adjusted using a locking mechanism in the form of a receiving channel such that the components that are lockable with a collet or other locking feature. In accordance with the various embodiments, the travel range between the described zero and maximum profile positions can vary as selected for appropriate use of the anchor. Without any intent to limit the range of operation of the adjustment, for application with spinal screws, the range may include 0 mm to 20 mm, and more particularly 0 mm to 10 mm, including fractional increments therein, including 0.1, 0.2, 0.3, 0.4, 0.5, 1.0, 1.5, 2.0, 2.5 up to and through 20.0 mm. Of course, other increments and ranges of travel are possible and implementation thereof is well within the skill in the art.

Split Body Anchor with Axial Sliding Collet

Referring again to the drawings, FIG. 1 depicts an exemplary embodiment of a vertically adjustable anchor assembly 10. The assembly includes the generally conventional components of a rod fixation system 30 and a tapered bone screw 60 with a threaded shank portion 100 for engagement in bone and a spherical screw head 20 portion, the rod fixation system 30 including a tulip head 32 with a bore 33 for receiving the shank of the screw 60 and seating the screw head 20 and a generally U-shaped channel, a receiving seat 35, for receiving a rod 38, a compression washer 34 for contact between the screw head 20 and the rod 38, and a locking nut 36 for locking the anchor assembly 10 to the rod 38. FIG. 2 shows an alternate exploded view of the anchor assembly 10 components depicted in FIG. 1, wherein the components are described in further detail herein below. As shown in the drawings that include FIGS. 1-10, the screw 60 threaded shank portion 100 and anchor assembly 10 are lockable by the actuation of the anchor assembly 10 components whereby compression of complimentary features 235 and 330, as further described herein, at the distal ends of the coaxially engaged components 200 and 300 involves the sliding contact between the complimentary ramp shaped features 330 and 235 in a manner that displaces one or both of the distal ends of the mating extensions 220 and 230 away from the shared center axis and into compressive contact with the receiving channel 120 of the threaded shank portion 100 functioning like a collet to achieve fixed engagement of the anchor assembly 10 within the channel 120 at the height selected by the user.

Referring now to FIG. 3, the depicted embodiment of an anchor subassembly screw 60 according to the invention specifically includes the novel elements of a modular screw 60 wherein the engagement and locking is achieved by compression of mating screw head 20 components that include a screw head proximal component 200 and a screw head distal component 300, respective proximal and distal hemispherical heads 210 and 310, and respective proximal and distal mating extensions 220 and 320, and a threaded shank portion 100. The screw head 20 and threaded shank portion 100 are each adapted for interconnection along a common elongate axis to form a screw 60 having a hemispherical screw head 20 and threaded shank portion 100 and the subassembly is capable of vertical displacement to achieve fixed or variable vertical height when implanted in a bone. In the depicted embodiment, the screw head 20 proximal and distal components 200 and 300 inter-engage to provide a slidable extension that includes engaged proximal and distal mating extensions 220 and 320 that are disposed at a distal end of the screw head 20, and the threaded shank portion 100 includes a hollow receiving channel 120 originating an opening disposed at its proximal end for receiving all or a portion of the proximal and distal components 200 and 300 of the screw head 20 therein. Partial engagement of the screw head 20 components 200, 300 by passage of the distal mating extension 220 of the proximal portion 200 into a through aperture 340 within the distal component 300 allows for vertical translation within the receiving channel 120. When the desired vertical position of the screw head 20 is selected, full engagement of the screw head 20 components 200 by compressive mating of the undersurface 260 of the proximal portion 200 head 210 into contact with the face 390 of the head 310 of the distal component 300 results in compression within the receiving channel 120 to fix the vertical position. Thus, the screw head 20 operates as a locking assembly. In some embodiments, the screw head 20 and threaded shank portion 100 components when fully engaged may become cold welded at their distal mating extensions 220 and 320 within the hollow receiving channel 120 because of compression, whereby disruption of metal surface oxide films results in adhesion between the components.

In various embodiments, the screw head 20 portion includes at least two components, comprising proximal and distal components 200 and 300, as shown in FIG. 4. FIGS. 5 and 6, respectively, show, in alternate views, the proximal and distal components 200 and 300 of the screw head 20 portion of the anchor assembly 10. As shown in the figures, these proximal and distal components 200 and 300 include at their proximal ends engageable proximal and distal hemispheres 210, 310 and distally they include mating extensions 220, 320 that are slideably engageable along a common axis to form a unitary, substantially spherical screw head 20 and a slidable extension formed with the engaged mating extensions 220, 320 that fits within a threaded shank portion 100, the extensions terminating in complimentary features 235 and 330 that cooperate to expand and lock within the threaded shank portion 100 when fully engaged as described herein. As depicted in FIG. 4, the proximal and distal hemispheres 210, 310 are defined by a horizontal split 22, such that one component includes an upper hemisphere 200 and the other component includes a lower hemisphere 300, the two mating at an essentially centerline position of a sphere when fully engaged. Other head shapes are possible, and the head may be split other than horizontally into the upper and lower hemispheres 210, 310.

Further, though the description herein refers to the portions of the head as being hemispheres, they may have other shapes that may form a shape other than a sphere when joined, for example a hex shape or an ovoid shape, and in other examples they may have a shape that is not enlarged relative to the distally extending portions of the components. Accordingly, in such alternate embodiments, the screw head 20 proximal and distal components 200, 300 may be varied such that neither component includes a hemispherical head, or only one component includes a hemispherical head. In accordance with such embodiments, a component 200, 300 that lacks a hemispherical head at its proximal end may have a head having another shape, and in certain embodiments, the head may be generally cylindrical, or it may be hex shaped, or it may have another shape adapted for engagement with a tool (not shown). Accordingly, in one such embodiment the screw head 20 portion of the anchor assembly 10 may include a proximal component 200 that has a generally cylindrical head at its proximal end and comprises a tool engagement feature that is adapted to inter-engage with a tool. The proximal component 200 inter-engages with the distal component 300 which has a hemispherical head 310 and may be passed either through the proximal aperture 340 of the distal component 300 or may be passed distally into the through aperture 340 since it lacks a hemispherical head that would interfere with passage from the distal end of the through aperture 340. In accordance with such embodiments, the tool engagement feature may be retained wholly within the proximal portion of the through aperture 340 of the distal component, or it may extend out of the through aperture 340 and beyond the face 390 of the hemispherical head 310 of the distal component 300. In use, the tool engagement feature of the proximal end of the proximal portion 200 may be gripped by a tool to actuate locking of the anchor assembly components 10 by pulling upward in a generally proximal direction while one of stabilizing the head of the distal component 300 (for example by retaining it within a tulip head) or by compression against the distal component 300 (for example in contact with the face 390) to effect compression within the through channel 120. It will be appreciated that in alternate embodiments, the distal component 300 may lack a shaped head such as a hemispherical head and the proximal component 200 may include a hemispherical head, and in some embodiments, each of the proximal and distal components 200 and 300 lack a shaped head such as a hemispherical head.

Referring again to FIG. 4, the proximal and distal mating extensions 220 and 320 are essentially non-equal halves of a cylinder, and in the depicted embodiment have an overall circular cross section. In alternate embodiments, the cross section of the extension may be hexagonal, ribbed, scalloped, ovoid, star shaped, square or another regular or irregular shape that is adapted to be slideably engageable with a receiving channel 120 in a threaded shank portion 100 or other receiver. For example, referring to FIG. 8, the slidable extension formed by the proximal and distal mating extensions 220, 320 is generally hex shaped, in contrast to the generally cylindrical shape of the embodiments shown in the preceding figures.

Figure 38:
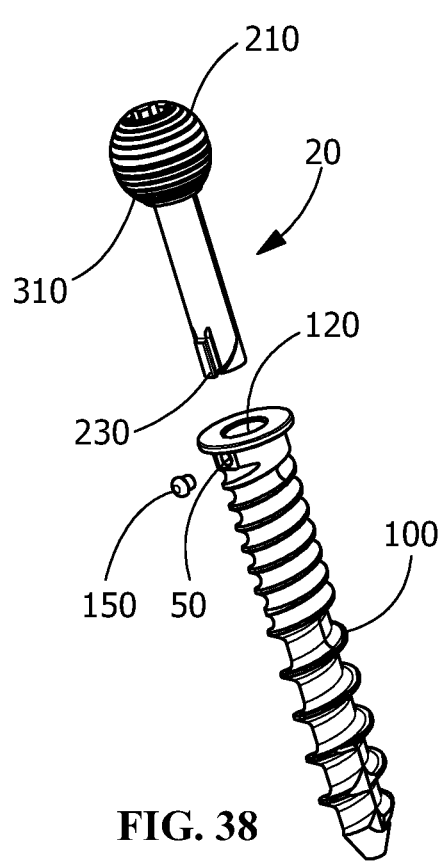
FIG. 38 shows a view of the anchor subassembly and the engagement pin shown in FIG. 1

FIGS. 28-37 show a variety of front, back, top, bottom, respective side and isometric views of the proximal and distal components 200 and 300 of the head 20 portion of the anchor assembly 10; FIG. 38 shows a view of the anchor subassembly 10 and the engagement feature 230 described herein below with reference to FIG. 1.

In some embodiments, the anchor assembly 10 also includes engagement features on one or more of the threaded shank portion 100 and the proximal and distal components 200 and 300. As shown in FIG. 5, for example, the proximal component 200 includes on the distal head mating extension 220 a first engagement feature 230, depicted in FIG. 5 as a boss or pin that engages with a slot (140 as described herein-below) in the receiving channel 120 in the threaded shank portion 100 (see FIG. 7, that shows a slot 140 that originates on the interior wall near the proximal end of the threaded shank portion 100 for receiving the engagement feature 230). In the depicted embodiment, the engagement feature 230 is positioned near the distal end of the distal mating extension 320 portion of the distal component 300. In alternate embodiments, the position of the engagement feature 230 may be varied along the length of the extension and may be more proximal. Likewise, the overall length of the extension may be varied. Further, the boss may instead be positioned within or inserted through a side channel slot 140 through the threaded shank portion 100 and an extension on one or the other of the head components may include a receiving hole or channel (not shown).

Figure 7:
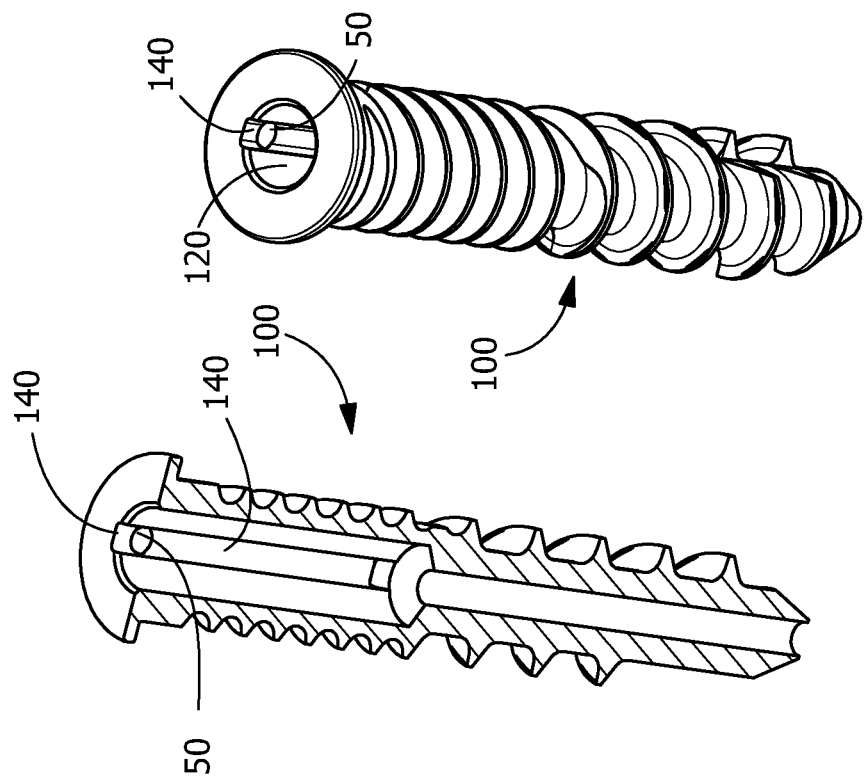
FIG. 7 shows alternate whole and cutaway views of a component of the subassembly shown in FIG. 3.

An additional engagement feature is shown in FIG. 1, and in more detail in each of FIGS. 2, 3 and 7. Referring now to FIG. 1, a perspective view of the assembly shows a locking seat 50 that is a substantially circular through bore within the proximal end of the threaded shank portion 100, the locking seat 50 adapted to receive a locking pin 150 that can be inserted in the locking seat 50. In use, the locking seat 50 and locking pin 150 operate to mate and lock with one another to prevent pullout of the proximal and distal mating extensions 220, 320 from the receiving channel 120 by blocking the upward translation of the boss engagement feature 230 within the slot 140, thereby fixing the upper limit of vertical translation of the head 20 relative to the threaded shank 100 portions of the screw 60.

In use, the boss engagement feature 230 and slot 140 engagement provides at least three functions, including temporary retention of the head component in the receiving channel 120 of the threaded shank portion 100, prevention of rotation of the engaged proximal and distal head mating extensions 220, 320 around the central axis, and bounding the upper and lower limits of the vertical range of travel of the proximal and distal mating extensions 220, 320 within the receiving channel 120 of the threaded shank 100, allowing for retention of engagement of the subassembly during height adjustment of the screw head 20 relative to the threaded shank portion 100.

The locking collet engagement feature 230 is shown in FIGS. 4 and 6. Referring to FIG. 6, distal mating extension 320 includes a distal foot 330 that is depicted in the drawings as cannulated (the foot is generally crescent shaped with a cylindrical cannula) with an angled incline that enhances the locking engagement of the proximal and distal components 200 and 300 when fully compressed. FIG. 1 shows a view of the fully engaged distal mating extensions 220, 320 showing the contoured engagement of the angled distal foot 330 of the distal mating extension 320 with a tapered and angled distal end taper 235 of the proximal mating extension 220. As depicted, the distal foot 330 is positioned on the distal mating extension 320 and the taper 235 is located on the proximal mating extension 220. In alternate embodiments, other combinations of these features are possible. In addition, the distal foot 330 and taper 235 are shown as cylindrical shaped in cross section in FIG. 1 and as hex shaped in cross section in FIG. 8. Of course, other shapes are possible. And in alternate embodiments the component having the distal foot 330 and the component having the taper 235, respectively, may be different than is shown in the depicted embodiments. In use, the proximal and distal mating extensions 220, 320 inter-engagement as described herein operate to provide controlled retention of the head components within the threaded shank portion 100 during selection of vertical positioning. Upon compression of the heads of the components 200 and 300, shown in the drawings as hemispheres 210, 310, together and locking of the proximal and distal mating extensions 220, 320, the engagement features, including but not limited to the engaged distal foot 330 and taper 235 lock by displacement of one or both the foot 330 and the taper 235 radially away from the center axis and into compression within the threaded shank through channel 120 and operate to enhance locking by preventing axial rotation and potential back out of the engaged proximal and distal components 200, 300 from within the threaded shank portion 100. In some embodiments, the proximal mating surfaces of the screw head 20 components may also be spring loaded to maintain separation until locking and to enhance and secure locking upon compression.

It will be appreciated that in alternate embodiments different or additional engagement features may be used that achieve the fixed engagement between subcomponents. Such engagement is useful to enable torsional engagement and actuation, such as with a driving tool of one or more components while preventing other components from experiencing torsional force. Likewise, it is advantageous to employ engagement features that serve as stops to prevent disengagement of components by the application of shear force, such as pull out of axially aligned components.

Referring again to FIG. 4, each of the respective head components includes features to provide adjustable and locking fixation within the receiving channel 120 of the shaft portion through action of the collet engagement feature that includes the distal foot 330 and taper features.

In use, the proximal and distal components 200, 300 are mated in a partially engaged manner, as depicted in FIG. 4, whereby they are not compressed and can be easily inserted into the shaft portion. According to the depicted embodiments, alignment can be achieved using the boss on the distal mating extension 320 and the slot 140 in the shank portion receiving channel 120. When the locking pin 150 is fixed in its locking seat 50, the screw head 20 is fixed in the shank 100. After the desired axial position (height) of the screw head 20 is determined, the proximal and distal components 200, 300 are compressed together resulting in relative expansion of the diameter of the proximal and distal mating extensions 220, 320 to actuate the collet locking function to provide circumferential expansive force of the extensions against the inner wall of the shaft receiving channel 120, thereby fixing the vertical position of the head portion within the shaft portion. It will be noted that the length of the receiving channel 120 establishes the maxim depth that the head portion can be inserted into the shaft portion, while the vertical extent (length) of the slot 140 in the receiving channel 120 establishes the range of vertical motion that is possible when the anchor includes the slot 140 and pin engagement feature 50 and 150. It will be appreciated that these features are optional, and may be varied or substituted with other features that control the range of vertical translation of the head relative to the shaft.

Referring again to FIG. 4, the proximal and distal components 200, 300 are each cannulated, and include a proximal component cannula 250 that has a relative width dimension that is greater than one half of the overall dimension of the assembled cylindrical extension that is formed by the engaged proximal and distal mating extensions 220, 320. Moreover, the proximal mating extension 220 is adapted with a bevel at its distal end to abut the distal foot 330 of the distal mating extension 320 so that the proximal component 200 it is compressed along its length relative to its mated lower hemisphere extension when subjected to the locking forces of the rod 38 in the fully assembled and locked state. The overall relative thickness of the upper hemispherical extension, when compressed lends resistance to the assembly bending off-axis when implanted in bone, particularly when the screw head 20 is in a greater vertical extension position within the shank portion 100. In addition, each of the head components includes flats 270 and 370 at the interfaces of the proximal and distal mating extensions 220, 320, to aid in stability and to prevent on-axis rotation of the head component when the screw is being driven into bone.

As described herein above, the various embodiments, including the representative embodiment in FIGS. 1-7 are adapted such that the vertical position of the anchor can be adjusted using a translation and locking mechanism wherein the travel range between zero and maximum profile positions can vary as selected by the surgeon for appropriate use of the anchor. Without any intent to limit the range of operation of the adjustment, particularly for applications with spinal screws, the range may include 0 mm to 20 mm, and more particularly 0 mm to 10 mm, including fractional increments therein, including 0.1, 0.2, 0.3, 0.4, 0.5, 1.0, 1.5, 2.0, 2.5 up to and through 20.0 mm. Of course, other increments and ranges of travel are possible and implementation thereof is well within the skill in the art. Accordingly, with reference to the embodiment of FIGS. 1-7, the screw head 20 is slidable within the threaded shank portion 100 within a desirable range of travel as described herein above or as otherwise established.

It will be appreciated that in each of the various embodiments according to the invention as shown in any of the FIGS. 1-7 herein, more than one modular adjustable anchor may be provided in the context of an otherwise conventional pedicle screw and rod system, wherein one or more modular adjustable anchors allow for an expanded range of vertical height adaptability at the various spinal levels treated with the system. The modular adjustable assemblies are particularly advantageous in that they provide options for providing preassembled bottom and top loading anchor assemblies, as well as anchor assemblies and subassemblies that may be assembled partially by the manufacturer or partially or completely by the surgeon, to achieve maximal flexibility in the surgical setting and customized treatment of the clinical subject.

Second Embodiment of Split Body Anchor with Axial Sliding Collet

Referring again to the drawings, an alternate embodiment of an adjustable anchor assembly is shown in FIG. 8. The depicted anchor assembly includes a plurality of essentially co-axial components that are assembled and can be locked together and is similar to the previously described embodiment.

Figure 9:
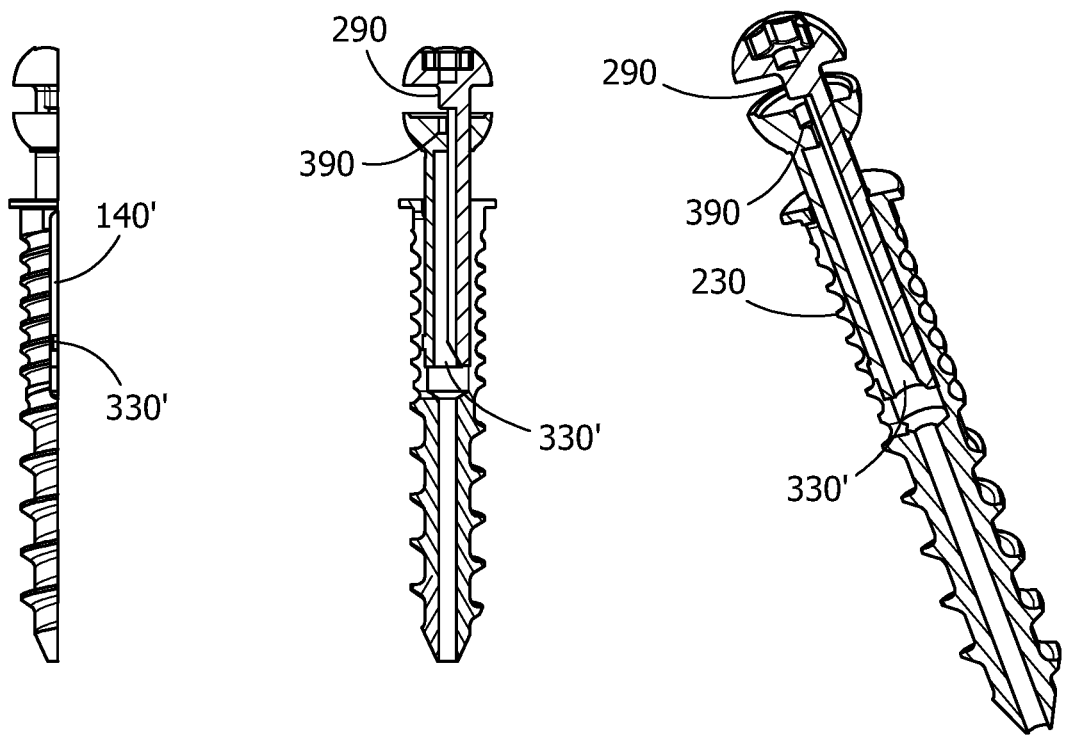
FIG. 9 shows alternate views of the assembly shown in FIG. 8.
Figure 10:
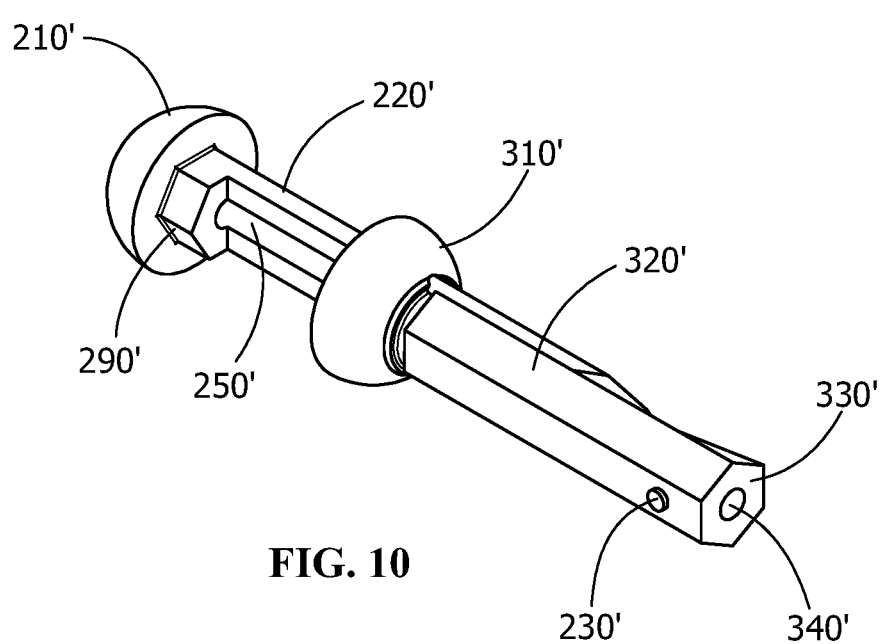
FIG. 10 shows alternate views of the assembly shown in FIG. 8.

Referring now to FIGS. 8-10, various states of assembly of an exemplary embodiment of a vertically adjustable anchor assembly are shown. The assembly includes the generally conventional components of a tapered bone screw with a threaded shank for engagement in bone and a spherical head, a tulip head with a bore 33 for receiving the shank of the screw and seating the screw head and a generally U-shaped channel, receiving seat 35, for receiving a rod, a compression washer 34 for contact between the screw head 20 and the rod 38, and a set screw or locking nut 36 for locking the anchor assembly 10 to the rod 38. FIG. 8 shows alternate exploded and end views of the anchor assembly components. FIGS. 9 and 10 show alternate views of the screw subassembly including various views of partial engagement of the head and shank components that are described in further detail herein below.

Referring now to FIGS. 8-10, the depicted embodiment of an anchor according to the invention specifically includes the novel elements of a modular threaded shank portion wherein the engagement and locking is achieved by compression of a mating screw head top and bottom portions and including an proximal component 200 and a distal component 300, each respectively having mating extensions 220 and 320, respectively. Vertical adjustment is achieved by translation along the shared vertical axis of the threaded shank portion 100. The screw head 20 and threaded shank portion 100 are each adapted for interconnection along a common elongate axis to form a screw having a spherical head and a threaded shank portion 100' and the subassembly is capable of vertical displacement to achieve fixed or variable vertical height when implanted in a bone. In the depicted embodiment, the screw head 20' components inter-engage to provide a slidable extension disposed at a distal end and the threaded shank portion 100' includes a hollow receiving channel 120' with an opening disposed at its proximal end for receiving all or a portion of the slidable extension therein. Partial engagement of the screw head 20' components allows for vertical translation within the receiving channel 120. When the desired vertical position of the screw head 20' is selected, full engagement of the screw head 20' components results in compression within the receiving channel 120' to fix the vertical position. In some embodiments, the screw head 20' and threaded shank portion 100' components are cold welded, whereby disruption of metal surface oxide films results in adhesion between the components.

In various embodiments, the screw head 20' portion includes at least two components. FIGS. 9 and 10 show, in alternate views, the alignment and mating of the screw head 20' components. As shown in the figures, these components include at proximal and distal components 200', 300' with hemispherical heads 210' 310' and mating extensions that are slideably engageable along a common axis to form a unitary, substantially spherical screw head and a slidable extension that fits within a threaded shank portion 100' or shank. As depicted, the hemispheres 210', 310' are defined by a horizontal split 22, such that one component includes an upper hemisphere 210' and the other component includes a lower hemisphere 310', the two mating at an essentially centerline position of a sphere when fully engaged. Other head shapes are possible, and the head may be split other than horizontally into upper and lower hemispheres 210', 310'. As depicted, the mating extensions 220', 320', are essentially equal halves of a cylinder, in the depicted embodiment having an overall hexagonal cross section. In alternate embodiments, the cross section of the extension may be circular, ribbed, scalloped, ovoid, star shaped, square or another regular or irregular shape that is adapted to be slideably engageable with a receiving channel 120' in a threaded shank portion 100' or other receiver.

In some embodiments, the anchor assembly 10' also includes engagement features on one or more of the threaded shank portion 100' and the head mating extensions 220', 320'. As shown in FIG. 10, for example, the distal component 3001 includes on the mating extension 320' a first engagement feature in the form of a boss or pin 230 that engages with a slot 140 within the receiving channel 120 in the threaded shank portion 100 (see FIGS. 8 and 9, side view that shows a slot 140' at the proximal end of the threaded shank portion 100' for receiving the boss). In the depicted embodiment, the boss is positioned near the distal end of the extension. In alternate embodiments, the position of the boss may be varied and the overall length of the extension may be varied. Further, the engagement feature may instead be positioned within or inserted through a side channel through the threaded shank portion 100 and an extension on one or the other of the proximal and distal head components 200', 300' may include a receiving hole or channel 120'. The depicted embodiment also comprises an additional engagement feature, as shown in FIG. 9, which includes a locking seat 390 within the distal component 300 adapted to receive a locking extension 290 from the proximal component 200, the locking extension 290 and locking seat 390 each respectively within the proximal and distal hemispheres 210, 310 of the proximal and distal components 200, 300, which operate by mating to lock and prevent independent axial rotation of the components. As shown, the locking extension 290 and locking seat 390, like the mating extensions 220, 320, are hex shaped in cross section. Of course, other shapes are possible in alternate embodiments and the component having the locking seat 390 and the component having the locking extension 290, respectively, may be different than is shown in the depicted embodiments.

The locking collet engagement feature is shown in FIGS. 9 and 10. Referring to FIG. 10, one extension component includes a distal foot 330' with an angled incline that enhances the locking engagement of the head components when fully compressed. FIG. 9 shows a side view of the mating extensions 220', 230' in a nearly complete compressed form, showing the contoured engagement of the angled distal foot 330' of the distal mating extension 320 with a tapered and angled distal end of the proximal mating extension 220. As depicted, the distal foot 330 is positioned on the distal component 300 and the taper is on the proximal component 200. In alternate embodiments, other combinations of these features are possible. In addition, the distal foot 330 and taper are shown hex shaped in cross section. Of course, other shapes are possible. And in alternate embodiments and the component having the distal foot 330 and the component having the taper, respectively, may be different than is shown in the depicted embodiments.

As described herein above, the various embodiments, including the representative embodiment in FIGS. 8-10 are adapted such that the vertical position of the anchor can be adjusted using a translation and locking mechanism wherein the travel range between zero and maximum profile positions can vary as selected by the surgeon for appropriate use of the anchor. Without any intent to limit the range of operation of the adjustment, particularly for applications with spinal screws, the range may include 0 mm to 20 mm, and more particularly 0 mm to 10 mm, including fractional increments therein, including 0.1, 0.2, 0.3, 0.4, 0.5, 1.0, 1.5, 2.0, 2.5 up to and through 20.0 mm. Of course, other increments and ranges of travel are possible and implementation thereof is well within the skill in the art. Accordingly, with reference to the embodiment of FIGS. 8-10, the screw head 20' is slidable within the threaded shank portion 100' within a desirable range of travel as described herein above or as otherwise established.

It will be appreciated that in each of the various embodiments according to the invention as shown in any of the FIGS. 8-10 herein, more than one screw component having a slidable extension may be provided, wherein such screw components are of varying lengths and therefore allow for an expanded range of vertical height adaptability. Whether the screw components are of fixed length or offered in ranges of lengths, such possible embodiments are particularly advantageous in that they provide options in some embodiments for providing preassembled bottom and top loading anchor assemblies, as well as anchor assemblies and subassemblies that may be assembled partially by the manufacturer or partially or completely by the surgeon, providing a range of options for achieving maximal flexibility in the surgical setting.

It will be appreciated that in alternate embodiments different or additional engagement features may be used that achieve the fixed engagement between subcomponents. Such engagement is useful to enable torsional engagement and actuation, such as with a driving tool, of one or more components while preventing other components from experiencing torsional force. Likewise, it is advantageous to employ engagement features that serve as stops to prevent disengagement of components by the application of shear force, such as pull out of axially aligned components.

Generally, in accordance with the embodiments depicted in FIGS. 8-10, the tulip head is merely representative of conventional designs, and is thus non-limiting to the extent that its function does not interfere with the operability of the vertically adjustable modular threaded shank portion. In accordance with the depicted embodiment, locking of the anchor assembly with the rod is achieved as with a conventional system, and the locking of the system is independent of the locking of the vertical position. Other features of the anchor assembly that may be conventional include features in the threaded shank portion that enable torque driven engagement within bone, which features are present on the terminal head portion of the threaded shank portion and can be actuated independent of the vertically adjustable collet feature. In some embodiments the engagement feature is a recess, such as a hex shaped recess for engagement with a hex driver, and in other possible embodiments the engagement feature is a positive structure that can be gripped by a suitable tool for rotation and torque driven engagement of the threaded distal portion with bone. It will be appreciated by one of skill in the art that the various embodiments described herein and depicted in the drawings are merely representative, and various elements thereof may be varied or interchanged to achieve the vertical translation contemplated to enable the benefits as described herein above.

Extendible Head Collet

Figure 11:
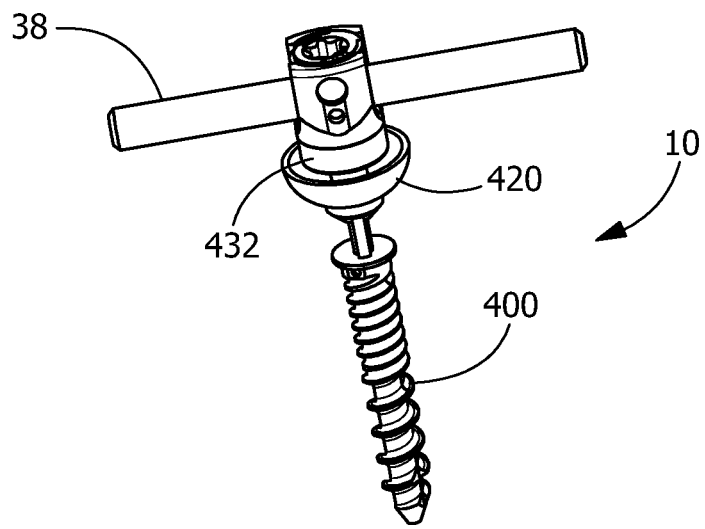
FIG. 11 shows alternate exploded and end views of the anchor assembly components of another embodiment disclosed herein.

Referring again to the drawings, an alternate embodiment of an anchor assembly is shown in FIG. 11. The anchor assembly includes a plurality of essentially co-axial components that are assembled and locked together. The depicted anchor assembly represents the general components of a pedicle screw used for vertebral fixation. The illustrated anchor assembly includes a seat or housing, typically referred to as a tulip head, having a bore for receiving a the shank of a screw there through and a receiving channel, a receiving seat, for engagement with a rod, a screw with a threaded shank and a generally spherical screw head that engages with the tulip head housing when the screw is positioned in the bore of the tulip head, a compression washer that engages the screw head and is contacted by the rod when the screw and rod are within the tulip head and functions to uniformly translate compressive force to the screw, and a locking nut or set screw that engages with the tulip head to secure the rod in its receiving seat 35 and lock the anchor assembly in connection with the rod. When assembled and engaged, the anchor assembly components are co-axial, as shown. It will be appreciated that fewer and varied elements of an anchor assembly may be used, including assemblies that are not adapted for use in the spine, without departing from the scope of the invention as it is directed to modular anchors and modular anchor assemblies suitable for fixation of a stabilization element to a bone.

In various embodiments, the anchor assembly may be provided for use by a surgeon in a pre-assembled state, completely disassembled, or in some state of subassembly. The system is adapted to function as poly-axial, uni-axial or mono-axial according to designs that are conventionally known in the art. In the various embodiments, screws can be of varying diameter, varying length, and can be cannulated or non-cannulated, fenestrated or non-fenestrated, tapered or non-tapered, self tapping or non-self tapping, and may have any of a variety of types of threading. Moreover, the assembly may be provided in a top- or bottom-loading format, wherein the screw component of the assembly is inserted into the tulip head either from the top or from the bottom, allowing in the instance of bottom loading screws, the ability of the surgeon to implant the shank of the screw and subsequently engage a selected screw head chosen from a selection that may vary in length or other feature, a selected stabilization element chosen from a selection that may vary in instrument attachment features, height or other feature, and combinations thereof. Examples of top and bottom loading tulip head configurations are generally known in the art as preassembled systems that are not typically adaptable within the surgical suite.

The anchor assembly can be a mono-axial, uni-axial or poly-axial, and in such various embodiments the assembly selected can allow for axial, and optionally multi-planar adjustment of the anchor. In the various embodiments, the vertically traveling height adjustable multi-planar screw includes a threaded shank portion including, for example, an external helical thread for penetrating bone through the application of torque. The upper portion of the threaded shank portion terminates in a screw head, which is generally spherical or hemispherical, and includes a feature suitable for engagement of a torque tool to achieve insertion into bone. The driving feature may be selected, for example, from a recess, or an extension, that is complementary to the shape of a tool or driver. An example of a recess feature is a hex head recess that is complementary to a hex head screwdriver. The anchor assembly components and rod can be formed from any suitable biocompatible material and combinations thereof, including those used conventionally in the art. Such materials include but are not limited to: metals such as, for example, stainless steel, titanium alloys, cobalt alloys, superelastic metals, such as nitinol; polymers, such as polyester and polyethylene, polyether ether ketone (PEEK); and resorbable synthetic materials such as, for example, suture material and polylactic acid.

In various embodiments, as shown in the figures, the anchor assembly includes modular components that are not present in conventional anchors and that engage to enable vertical modular implantation and adjustability by means of travel of the anchor components along the long axis of the screw to achieve varying heights. Generally, according to the invention, the anchor assemblies have features in common wherein the vertical position of the anchor is adjusted and the components that are lockable with a collet or other locking feature. In accordance with the various embodiments, the travel range between the described zero and maximum profile positions can vary as selected for appropriate use of the anchor. Without any intent to limit the range of operation of the adjustment, for application with spinal screws, the range may include 0 mm to 20 mm, and more particularly 0 mm to 10 mm, including fractional increments therein, including 0.1, 0.2, 0.3, 0.4, 0.5, 1.0, 1.5, 2.0, and 2.5 up to and through 20.0 mm. Of course, other increments and ranges of travel are possible and implementation thereof is well within the skill in the art.

Referring again to FIG. 11, various states of assembly of an exemplary embodiment of an extendible head collet with clamping-receiving channel adjustable anchor assembly are shown. The anchor assembly includes the generally conventional components of a tapered bone screw with a threaded shank for engagement in bone and a spherical head, a tulip head with a bore for receiving the shank of the screw and seating the screw head and a generally U-shaped channel for receiving a rod, a compression washer for contact between the screw head and the rod, and a set screw for locking the anchor assembly to the rod. FIGS. 11 A, B and C, respectively show, an exploded view, a partially assembled and an assembled view of certain of the anchor assembly components (the exploded and partially assembled views of FIGS. 11 A and B lacking the rod and the set screw, and FIG. 11 C showing the fully assembled anchor assembly wherein the rod is locked in place with the set screw).

Referring again to FIG. 11, the depicted embodiment of an anchor according to the invention specifically includes the novel elements of a modular threaded shank portion wherein the engagement and locking is achieved with a collet. According to the depicted embodiment, the screw is non-unitary, and includes a screw head portion including a spherical screw head and a separate threaded shank portion including a threaded shank. The threaded shank portion of the screw includes a non-threaded slidable extension adapted to mate with the receiving channel within the elongate receiving channel of the spherical screw head. The anchor assembly also includes the novel element of a compression seat 420, and as depicted in the Figures the compression seat 420 is generally bowl shaped and includes a compressive ring that engages with the anchor assembly in a coaxial arrangement.

In accordance with various embodiments according to the invention, for example as depicted in the embodiment in FIG. 11, vertical adjustment is achieved by translation along the shared vertical axis and locking is achieved via a collet. The spherical screw head portion includes a hollow receiving channel extension that includes at least one vertical slit along at least a portion of its length. Referring now to FIG. 11, as depicted, the elongate receiving channel of the screw head includes a plurality of vertical slits arranged generally symmetrically around its circumference, each slit running from the distal end and terminating proximally at the base of the sphere. In operation, circumferential compression of this collet feature of the screw head enables compression and/or frictional engagement with a slidable extension inserted there through.

The compression seat 420, as shown, is seated in a coaxial arrangement around the elongate receiving channel of the screw head and is adapted to travel in a vertical dimension between the distal and proximal ends of the screw head collet. As depicted, the collet terminates at its distal end in tab type head extensions (flanges) that serve to engage the base of the compression seat thereby fixing it on the screw head and preventing it from sliding off the distal foot of the collet. Further, the collet includes a plurality of locking protuberances (flanges, bosses or tabs) arranged between its distal and proximal ends, the tabs distributed in a circumferential arrangement around the collet.

Referring again to FIG. 11, in its unlocked configuration, the compression seat 420 is positioned at the proximal portion of the collet, above the locking protuberances and is retained in this position and restrained from downward vertical travel by the protuberances. In the unlocked position, the compression seat 420 does not exert any compressive force on the collet, thus allowing for the collet to remain in an essentially fully-open configuration permitting free vertical movement of the non-threaded slidable extension of the threaded shank portion within the collet channel when inserted therein. In use, the collet is slideably engaged on the slidable extension of the threaded shank portion 450, and is capable of travel between a zero profile position, wherein the slidable extension is fully inserted in the collet, and a maximum profile position wherein the slidable extension is inserted at the extreme distal portion of the collet.

Figure 12:
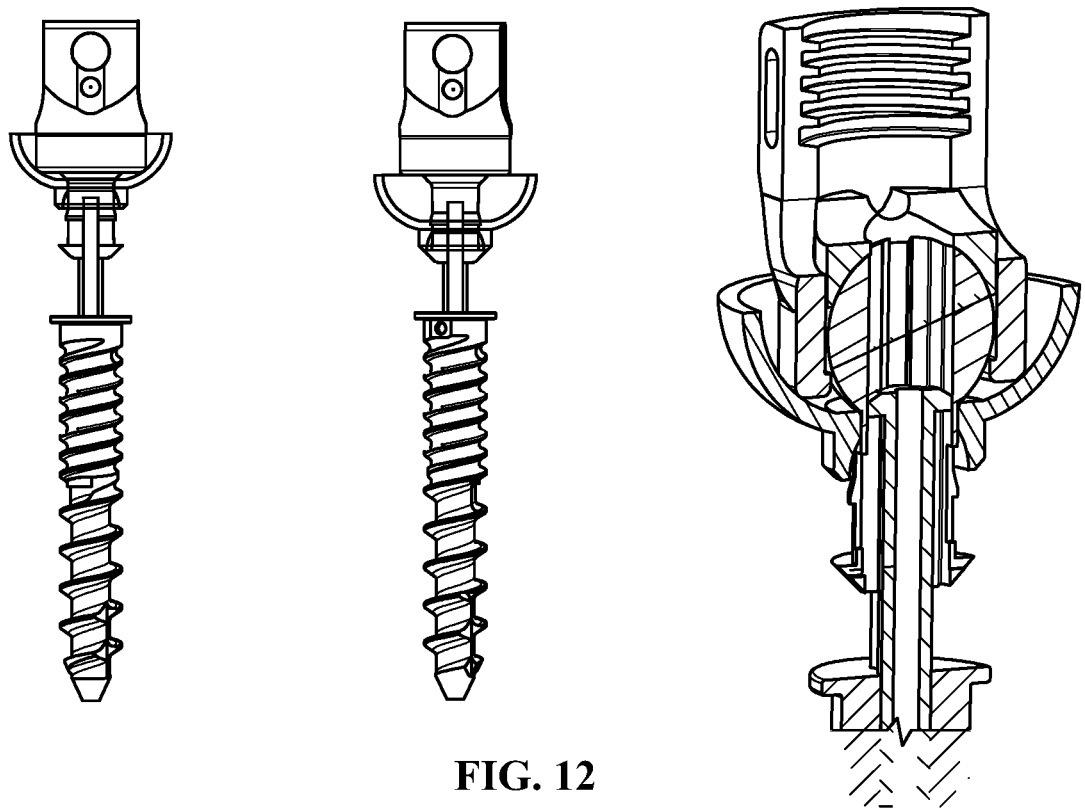
FIG. 12 shows alternate views of the assembly shown in FIG. 11.

Locking of the desired vertical position is achieved by sliding the compression seat 420 over the locking protuberances and into the locked position between the locking protuberances and the lower flanges. This engagement of the compression seat 420 results in the collet achieving a fully-closed position whereby it is compressed and/or frictionally locked to the threaded shank portion. FIGS. 12 and 13 provide additional detail showing the structural features of the components of the depicted embodiment, including the structural elements of the collet channel and corresponding threaded shank portion that enhance engagement thereof and prevent rotational movement of the screw head collet around the common axis.

It will be appreciated by those skilled in the art that the embodiment of the anchor in accordance with the invention that is depicted in FIGS. 10-13 is merely representative of a modular design that is vertically adjustable and lockable with a collet. In some embodiments, the collet may be formed of more or fewer slots, and such slots may be arrayed in a different arrangement around the circumference of the collet, and in various examples travel only a portion of the distance between the proximal and distal ends of the collet. For example, there may be a plurality of slots, wherein one or more of each such slots travels from the proximal end and terminates before the distal end, and wherein one or more travels from the distal end and terminates before the proximal end, and wherein one or more travels from a proximal point below the spherical screw head and terminates at a point before the distal end, and combinations of these.

In various embodiments of anchors in accordance with the invention, specific features of the collet, head extensions, and compression element may vary, wherein the collet element may be on the screw head as shown in FIGS. 10-15, the heads shown as 20', 420, 520 and 620, respectively, engageable with shanks shown as 100', 400, 500, 600 and 700, respectively, and wherein the collet element may be on the threaded shank portion, such that the proximal portion of the threaded shank portion 750 and 850, respectively, and is adapted to receive a slidable extension screw head 720 or 820, as shown in FIGS. 16 and 17.

According to some embodiments, the collet and slidable extension may have different mating features that facilitate alignment and prevent non-axial rotation, or they may lack such features. Further, in various embodiments, the form and shape of the compression element may vary such that compression is achieved with a snap fit ring, or clip, and in some embodiments the compression may be achieved with a ring or sleeve that substantially encloses the collet. FIG. 15 shows a representative embodiment wherein compression is achieved using an exterior ring in the form of a threaded nut that engages with threads on the exterior of the threaded shank portion to compress the threaded shank portion into compressed and/or frictional engagement with a slidable extension of the screw head inserted in the threaded shank portion. FIG. 14 shows an anchor assembly having a similar means of compression, which is a variation on the embodiment in FIGS. 11-13, including a spherical head having an elongate receiving channel for receiving a slidable extension on the threaded shank portion module, and wherein a threaded nut screws on to a threaded distal portion of the screw head to achieve compression and/or frictional engagement with the threaded shank portion. Further, the features of the collet that engage with the compression element may vary and may include any one or more of features such as channels, grooves, slots, slits, bosses, ridges, and other textural engagement features, and any of a combination of these.

Generally in accordance with the embodiments depicted in the FIGS. 11-17, the tulip head is merely representative of conventional designs, and is thus non-limiting to the extent that its function does not interfere with the operability of the vertically adjustable modular threaded shank portion. In accordance with the depicted embodiment, locking of the assembly with the rod is achieved as with a conventional system, and the locking of the system is independent of the locking of the vertical position. Other features of the anchor assembly that may be conventional include features in the threaded shank portion that enable torque driven engagement within bone, which features are present on the terminal head portion of the threaded shank portion and can be actuated independent of the vertically adjustable collet feature. In some embodiments the engagement feature is a recess, such as a hex shaped recess for engagement with a hex driver, and in other possible embodiments the engagement feature is a positive structure that can be gripped by a suitable tool for rotation and torque driven engagement of the threaded distal portion with bone.

Turnbuckle/Worm Gear Driven Embodiments

Figure 19:
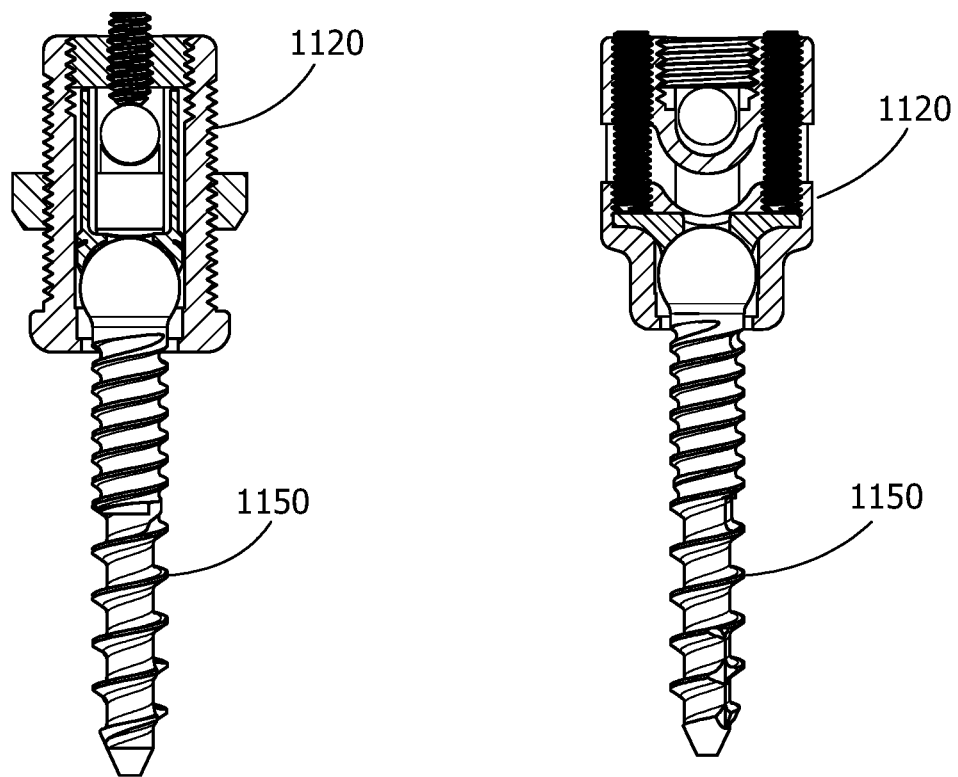
FIG. 19 shows an alternate embodiment of the anchor assembly as disclosed herein.

Referring now to FIGS. 18 left and right, and 19 left and right, various states of assembly of four exemplary anchors are shown wherein each depicted anchor includes modular components of either or both the screw and the tulip head, and wherein an engagement element operates to achieve vertical translation of the modular elements. In the figures, the vertical translation element is shown as elements 920 and 1020, respectively, each of which engages with the head of a screw (show as spherical) with its elongate shank show as 950, 1050, respectively. In some embodiments, the operation of the engagement element includes features of a turnbuckle, wherein the engagement element is internally threaded at both ends into which threads the corresponding sections of two threaded screw modules are engaged in order to form a unit that can be adjusted to achieve adjustable vertical height. In some alternative embodiments, the operation of the engagement elements may include features of a worm gear, wherein the engagement element may be actuated to drive the movement of a threaded gear that effects vertical translation of the modular components and wherein the gear cannot turn the engagement element thereby operating to effectively lock the modules in the selected vertical position. Such embodiments are shown in FIG. 19 left and right.

Figure 20:
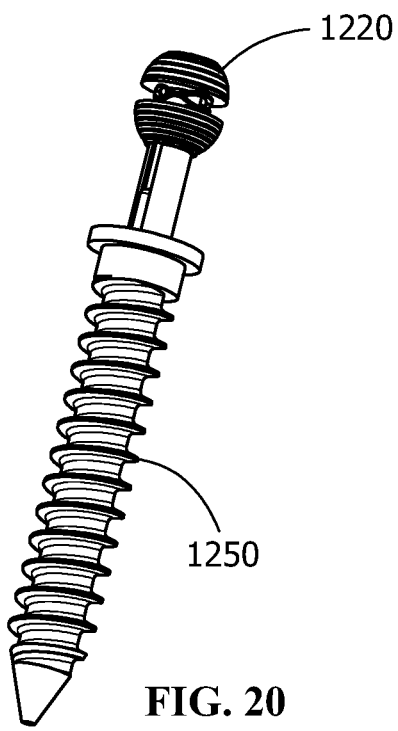
FIG. 20 shows an alternate embodiment of the anchor assembly as disclosed herein.
Figure 21:
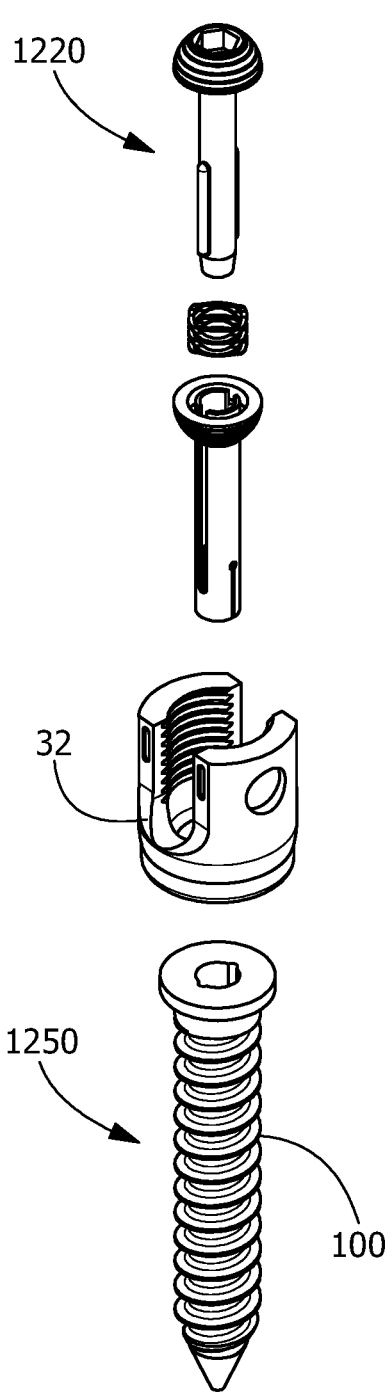
FIG. 21 shows alternate views of the assembly shown in FIG. 20.
Figure 22:
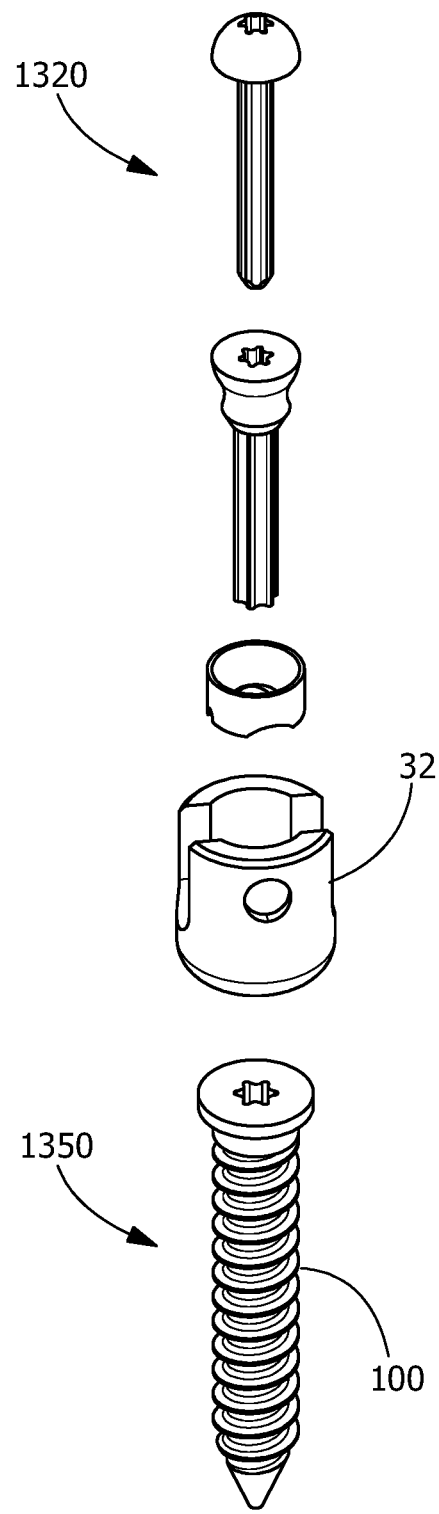
FIG. 22 shows an alternate embodiment of the anchor assembly as disclosed herein.
Figure 24:
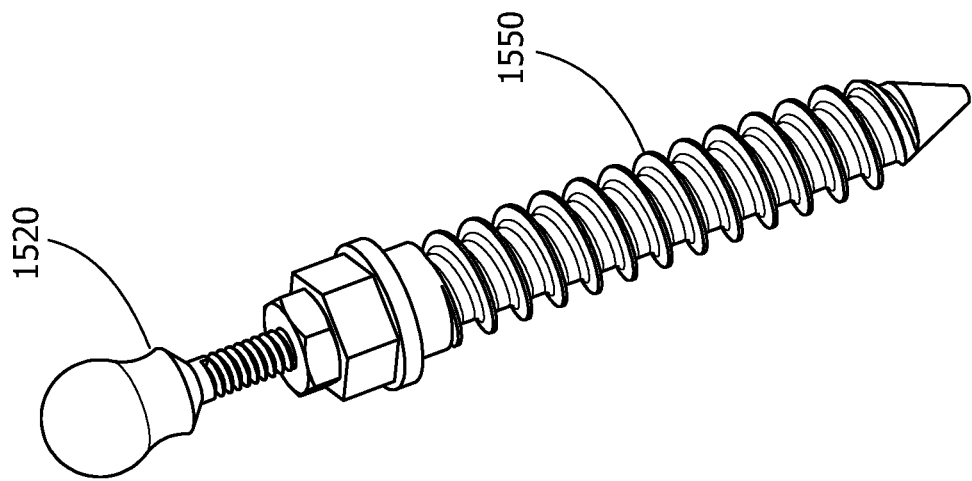
FIG. 24 shows an alternate embodiment of the anchor assembly as disclosed herein.
Figure 23:
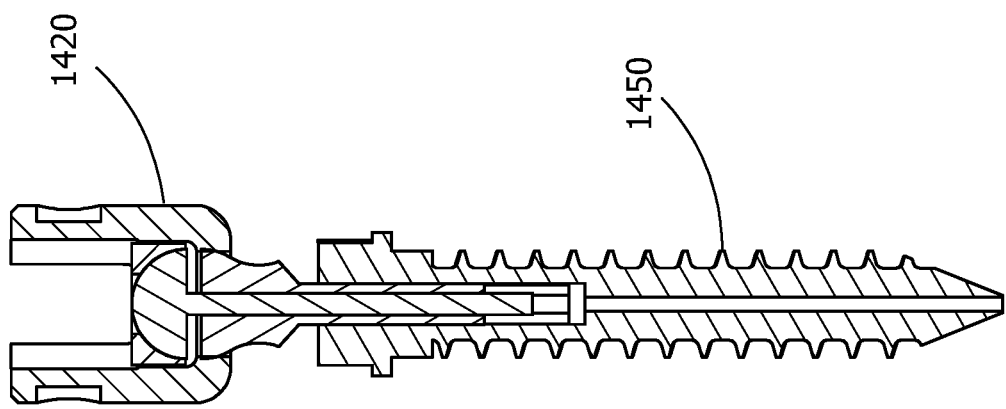
FIG. 23 shows alternate views of the assembly shown in FIG. 22.
Figure 25:
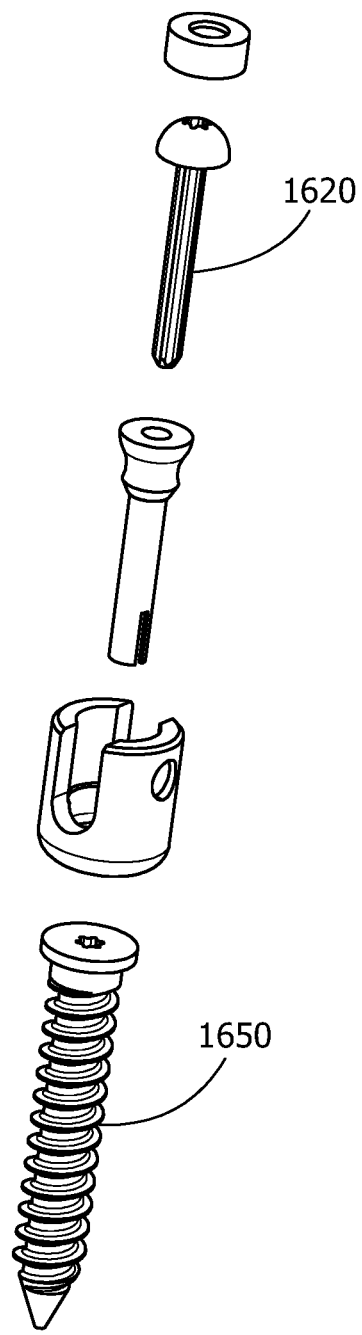
FIG. 25 shows alternate views of the assembly shown in FIG. 24.
Figure 26:
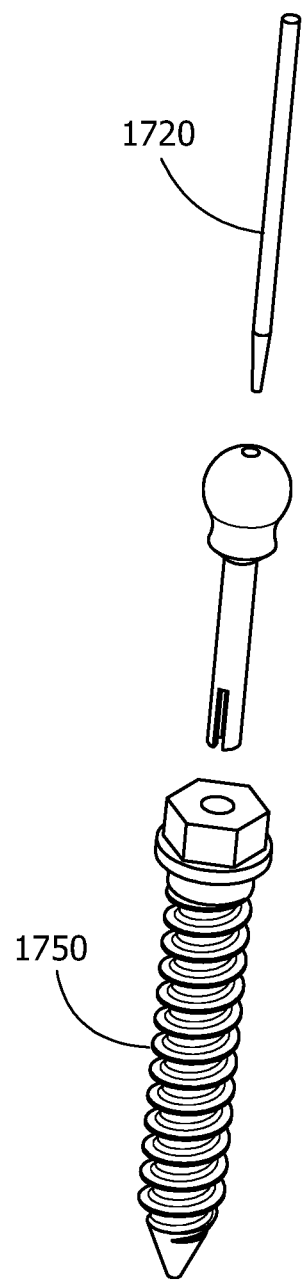
FIG. 26 shows an alternate embodiment of the anchor assembly as disclosed herein.
Figure 27:
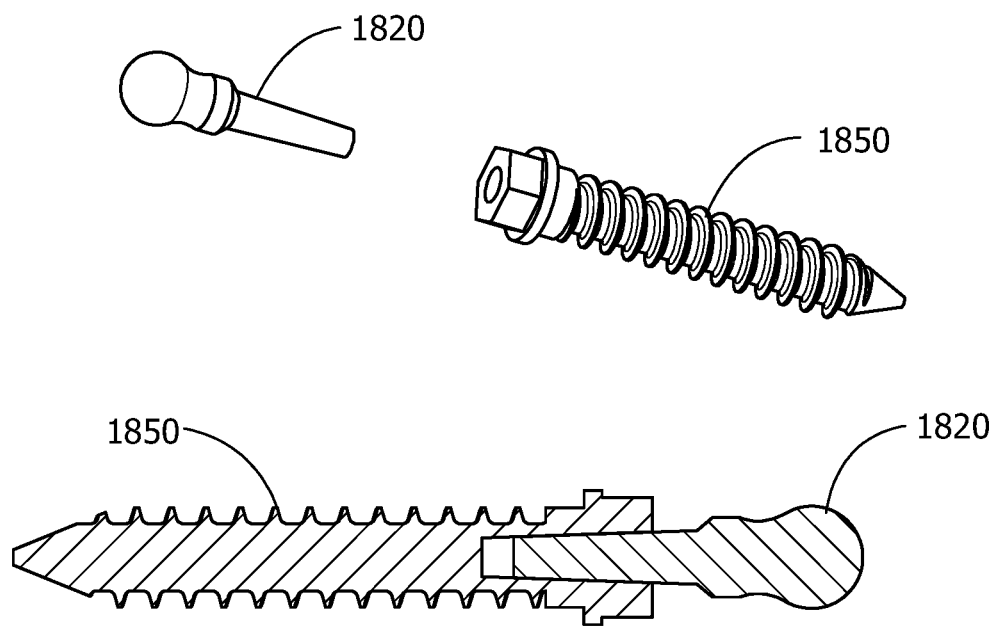
FIG. 27 shows an alternate embodiment of the anchor assembly as disclosed herein.
Figure 28:
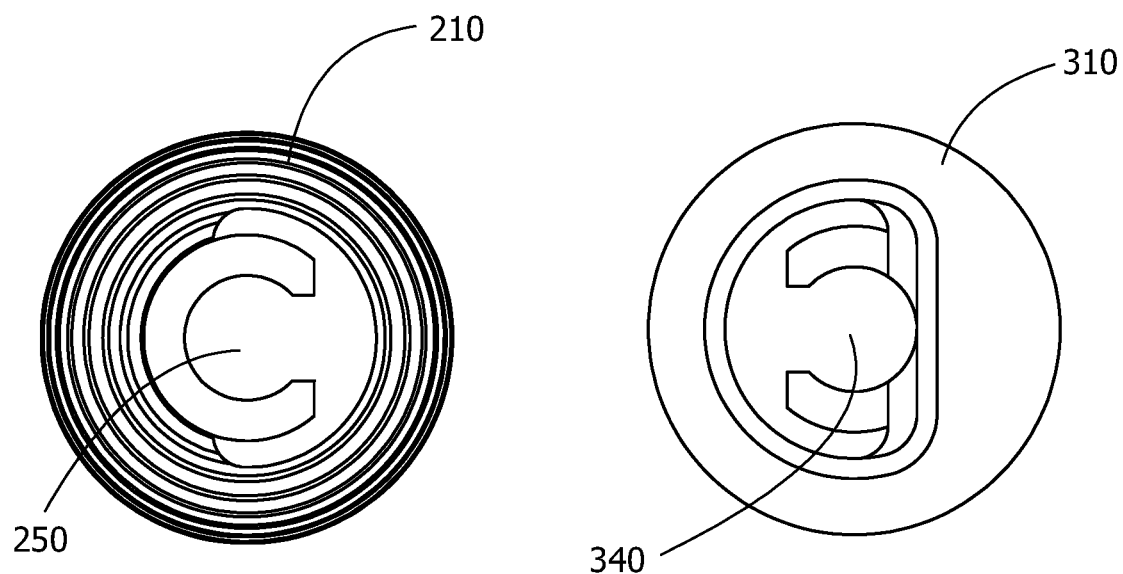
FIG. 28 shows respective proximal and distal end views of the assembly component shown in FIG. 6.
Figure 29:
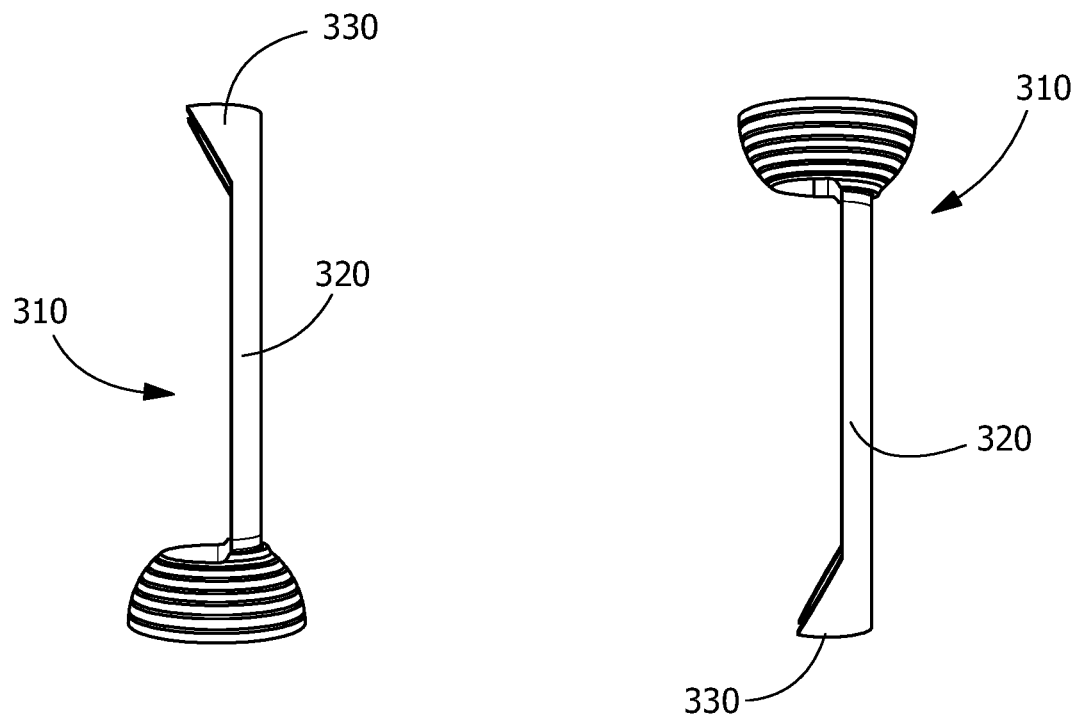
FIG. 29 shows respective side views of the assembly component shown in FIG. 6.
Figure 30:
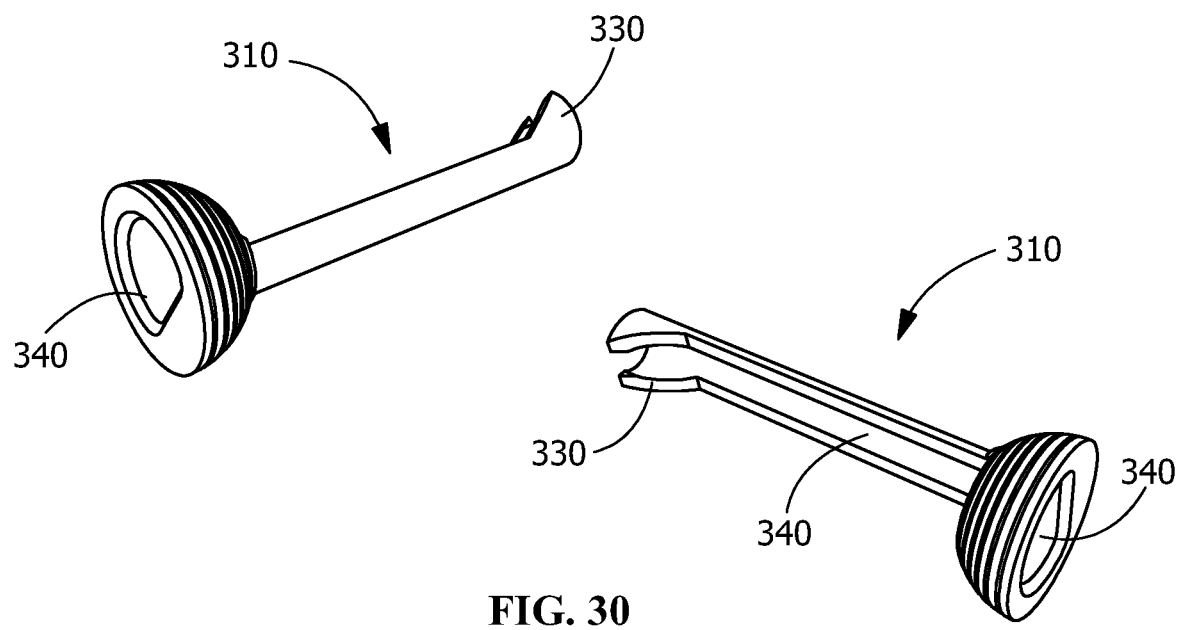
FIG. 30 shows alternate side perspective views of the assembly component shown in FIG. 6.
Figure 31:
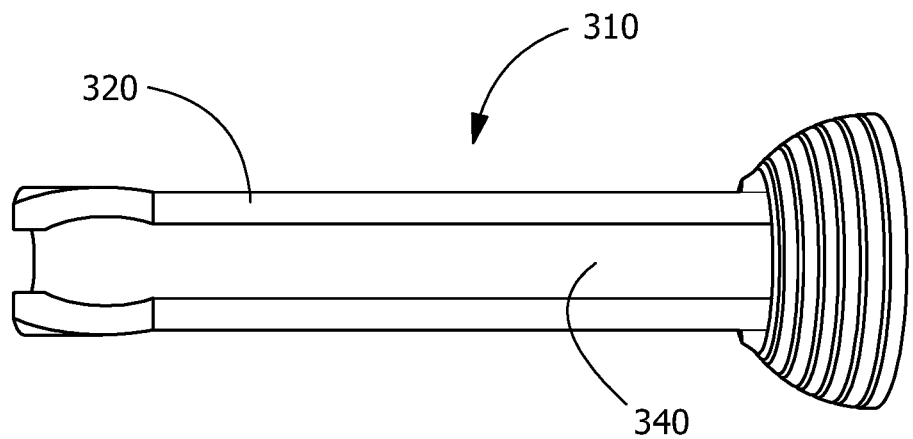
FIG. 31 shows a side view of the assembly component shown in FIG. 6.
Figure 32:
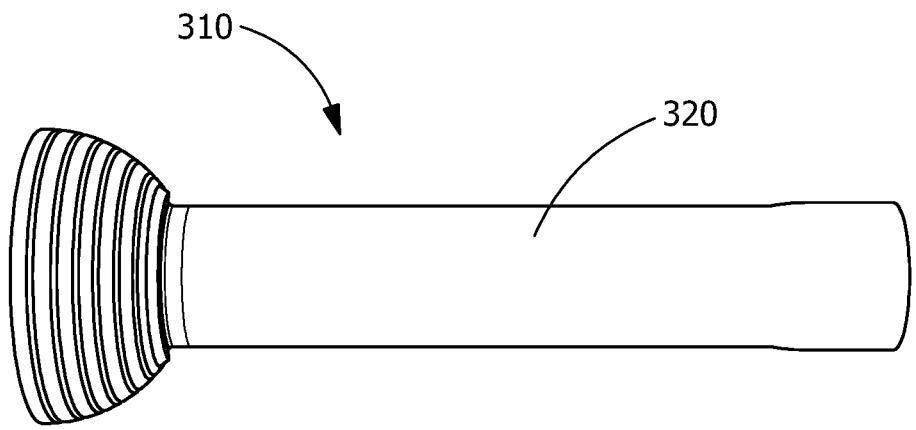
FIG. 32 shows a side view of the assembly component shown in FIG. 6.
Figure 33:
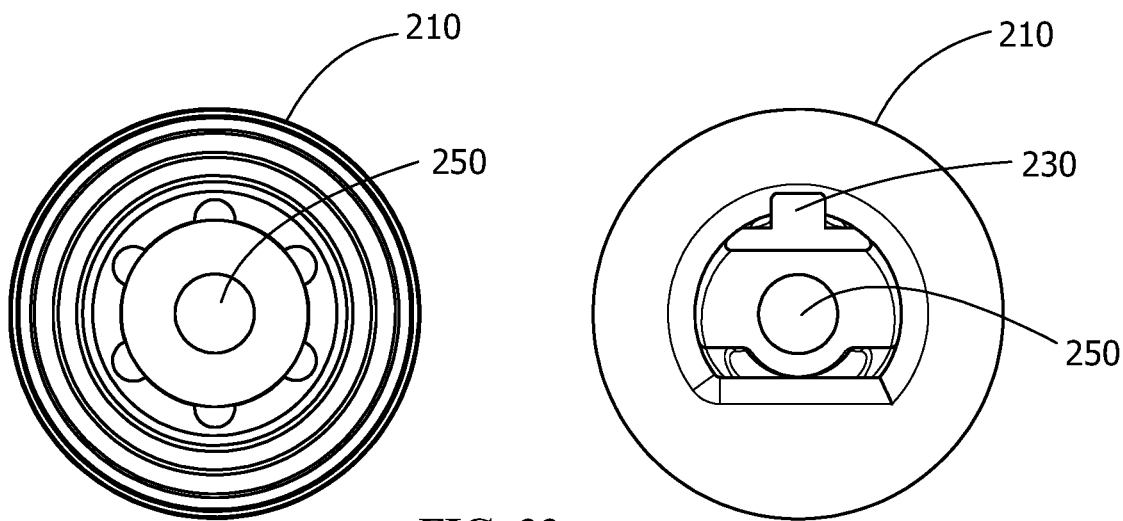
FIG. 33 shows respective proximal and distal end views of the assembly component shown in FIG. 5.
Figure 34:
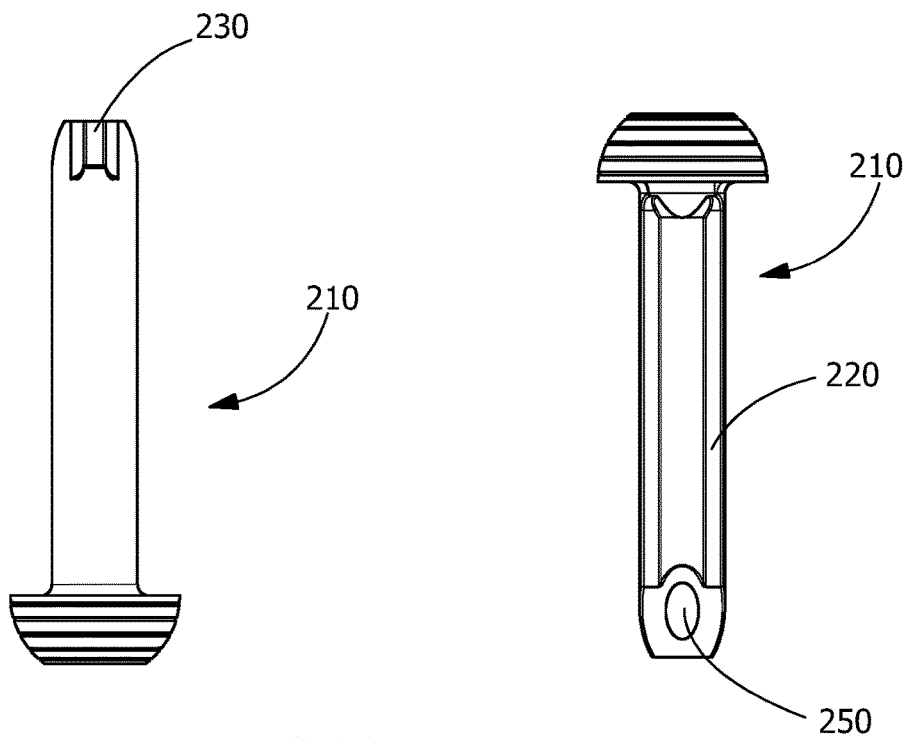
FIG. 34 shows respective side views of the assembly component shown in FIG. 5.
Figure 35:
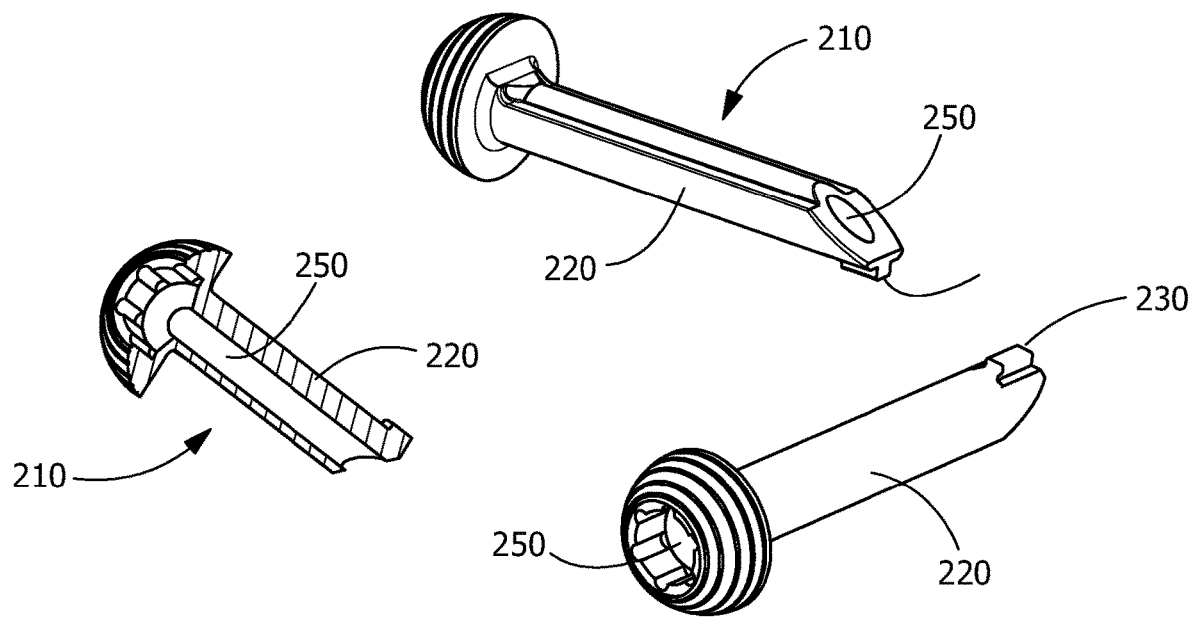
FIG. 35 shows alternate side perspective views of the assembly component shown in FIG. 5.
Figure 36:
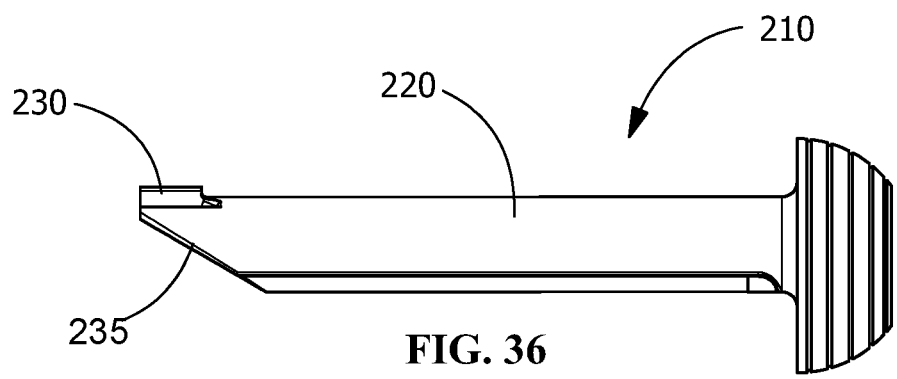
FIG. 36 shows a side view of the assembly component shown in FIG. 5.
Figure 37:
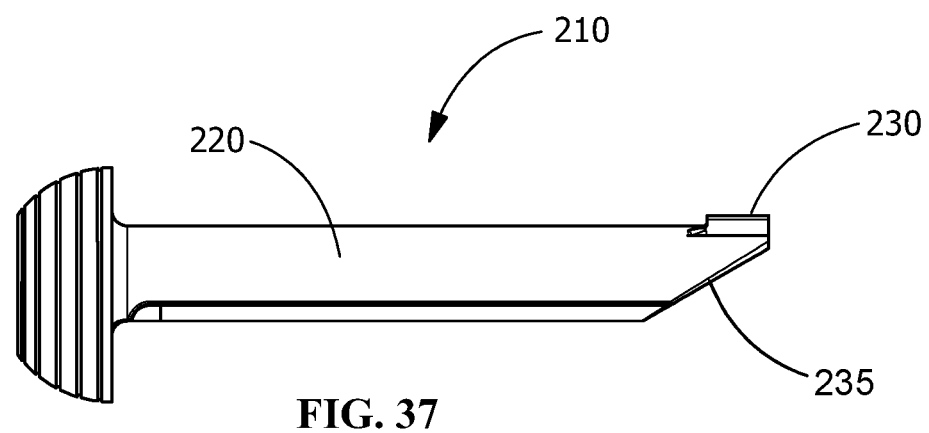
FIG. 37 shows a side view of the assembly component shown in FIG. 5.

Referring again to the drawings, an alternate embodiment of a modular and adjustable bone anchor for securing a bone stabilization element to a bone is depicted in FIGS. 20 and 21, and, as described herein above with respect to other embodiments, the depicted embodiment may be similarly varied in vertical height via adjustment of modular anchor elements and locking is achieved with a collet. In the figures, the vertical translation element is shown as 1220 which engages with the elongate shank 1250. As described herein above with respect to some conventional pedicle screw anchors, pressure from the rod locked into the tulip head by a threaded nut results in displacement of the compression washer within the tulip head and compression on the head of the screw thereby transferring compressive force onto the screw, fixing it into place within the tulip head and preventing any axial rotation (for uni- and poly-axial assemblies). This compressive force also serves to lock the collet thereby fixing the vertical position selected by the surgeon.

In accordance with the depicted embodiment, the components of the anchor assembly that achieve locking of the anchor to the rod can also actuate the collet locking mechanism for fixing the proximal portion of the anchor assembly to its distal portion and optionally fixing the vertical position of the anchor relative to the vertebra and the fixation system elements. Of course, in other embodiments, the means of achieving locking of the collet may be other than the locking means for fixation to the stabilization element, and in yet other embodiments the locking means may be the same but the specific elements, such as the compression washer, may be varied. FIGS. 20 and 21 show this alternate embodiment in alternative views. In accordance with the depicted embodiment, the anchor includes a head portion including at a proximal end a hemispherical screw head and a separate threaded shank portion including at a distal end a threaded shank. The screw head and threaded shank portions are adapted for interconnection along a common elongate axis to form a screw having a hemispherical head and threaded shank and the subassembly is capable of vertical displacement to achieve fixed or variable vertical height when implanted in a bone. In the depicted embodiment, the screw head includes a slidable extension disposed at its distal end and the threaded shank portion includes a hollow receiving channel extension disposed at its proximal end. The receiving channel is adapted to receive all or a portion of the slidable extension therein.

As described herein above, the various embodiments, including the embodiment in FIGS. 20 and 21 is adapted such that the vertical position of the anchor can be adjusted using a translation and locking mechanism wherein the travel range between zero and maximum profile positions can vary as selected by the surgeon for appropriate use of the anchor. Without any intent to limit the range of operation of the adjustment, particularly for applications with spinal screws, the range may include 0 mm to 20 mm, and more particularly 0 mm to 10 mm, including fractional increments therein, including 0.1, 0.2, 0.3, 0.4, 0.5, 1.0, 1.5, 2.0, 2.5 up to and through 20.0 mm. Of course, other increments and ranges of travel are possible and implementation thereof is well within the skill in the art. Accordingly, with reference to the embodiment of FIG. 20, the screw head is slidable within the threaded shank portion within a desirable range of travel as described herein above or as otherwise established.

It will be appreciated that in each of the various embodiments according to the invention as shown in FIG. 20, more than one screw component having a slidable extension may be provided, wherein such screw components are of varying lengths and therefore allow for an expanded range of vertical height adaptability. Whether the screw components are of fixed length or offered in ranges of lengths, such possible embodiments are particularly advantageous in that they provide options in some embodiments for providing preassembled bottom and top loading anchor assemblies, as well as anchor assemblies and subassemblies that may be assembled partially by the manufacturer or partially or completely by the surgeon, providing a range of options for achieving maximal flexibility in the surgical setting.

Referring again to FIGS. 20 and 21, such embodiment also includes a collet in the form of an elongate insert adapted for positioning along the common elongate axis of the head and threaded shank portions of the screw. The collet is adapted to receive insertion of the elongate extension and is insertable in the receiving channel of the shank portion and includes one or a plurality of vertical slits arranged along at least a portion of its length along the common elongate axis. Also included in such embodiments is a compression element adapted for direct engagement with the assembled screw, wherein the compression element is positionable between open and locked arrangements. When the slidable extension, collet and receiving channel are coaxially engaged and the slidable extension is at least partially inserted in the receiving channel extension, actuation of the compression element from the open arrangement to the locked arrangement compresses the collet against the coaxially arranged head extensions to achieve locking therebetween, thereby preventing further vertical travel between the screw portions.

It will be appreciated that a variety of conventional features of collets are known in the art and may be selected to facilitate locking and compression and/or frictional engagement between a collet and engaged anchor components. In some instances, variations in the thickness of walls of one or more components can be employed to achieve compressive engagement. In other examples, collet features may include tapers along the length of engaging components. It will be understood that the features described herein are intended to be non-limiting and other features of collets known in the art may be used to achieve the inventive modular and adjustable anchors in accordance with the invention.

In some embodiments, the anchor assembly also includes engagement features on one or more of the head extensions. As shown in FIG. 21, the slidable extension includes a first engagement feature that fixes alignment between the slidable extension, the receiving channel extension and the collet and can be actuated to prevent independent rotation of each of the slidable extensions, the receiving channel extension and the collet around the common elongate axis.

Referring again to FIG. 21, the slidable extension also includes a second engagement feature that is independent of the collet, wherein the second engagement feature fixes alignment between the slidable extension and the receiving channel extension and can be actuated to prevent vertical separation (pull out) of the slidable extension and the receiving channel extension. In some examples, as shown, the first engagement feature includes at least one elongate protuberance in the form of a ridge oriented along the common elongate axis that terminates at a point above the terminal end of the elongate extension. The collet includes a corresponding elongate slot, and the receiving channel extension of the threaded shank portion includes a corresponding elongate channel for receiving the first engagement feature. The second engagement feature includes at least one projection or boss positioned at the distal end of the slidable extension between the terminal end of the elongate extension and the terminal point of the first engagement feature and is offset from the first engagement feature, and wherein the receiving channel extension includes a corresponding channel for receiving the second engagement feature that is offset from the channel for receiving the first engagement feature, and wherein the second engagement feature is engageable with the receiving channel extension and is not engageable with the collet.

In use, the slidable extension and collet sub assembly are aligned and engaged, and upon their initial insertion in the receiving channel extension, the second engagement feature first engages with the corresponding channel of the receiving channel extension, and upon axial rotation thereof the second engagement feature travels within the channel to a point where the first engagement feature is in alignment with its corresponding channel. Upon further vertical advancement of the aligned slidable extension and collet within the receiving channel extension, each of the elements of the assembly is restricted from independent rotation around the common elongate axis and the assembly is restricted from vertical disengagement.

It will be appreciated that in alternate embodiments different or additional engagement features may be used that achieve the fixed engagement between subcomponents. Such engagement is useful to enable torsional engagement and actuation, such as with a driving tool, of one or more components while preventing other components from experiencing torsional force. Likewise, it is advantageous to employ engagement features that serve as stops to prevent disengagement of components by the application of shear force, such as pull out of axially aligned components.

According to the embodiments shown in FIGS. 20 and 21, the vertically adjustable bone anchor has a hemispherical head portion that engages with an opposing hemispherical head on the collet to substantially complete a spherical head on the screw head when the two are engaged. The assembly also includes a compression element in the form of a spring that that is axially engageable within one or both of the hemispherical portions of the collet and screw head. The spring serves to bias the hemispherical head of the screw head against the hemispherical portion of the collet. In the open arrangement, the screw is no more than partially compressed, thereby preventing full insertion of the slidable extension within the collet and thus preventing it from locking engagement within the threaded shank portion. In the closed or locked arrangement, the spring is fully compressed, and the slidable extension is fully inserted within the collet, thereby expanding the collet into compressed and frictional engagement within the receiving channel extension.

As described herein above, the depicted compression element shown in FIG. 21 is actuated by pressure from the spinal fixation assembly locking element. When in use, the anchor assembly is at least partially assembled, and the distal threaded end of the tapered screw is engaged in the bone. Upon full assembly of the bone screw and collet subassembly with the tulip head, placement of the compression washer and insertion of the rod, the assembly may be provisionally (temporarily) locked with the set screw. The vertical and axial arrangement of the anchor and other system anchors and the rod may be optimized. Thereafter, upon further tightening of the sect screw, the locking element is engaged in the retaining housing whereby compressive force from the locking element is transmitted to the rod, through the compression washer to the head of the screw thereby transferring compressive force onto the hemispherical head of the screw. This transmitted compressive force compresses the bias spring urging the hemispherical portions of the screw head and collet together, thereby locking the collet and fixing the vertical position of the anchor.

As described above, several of the features may be adapted without departing from the scope of the invention. For example, as shown in the FIGS. 20 and 21, the engagement features may be singular or a plurality and arranged in alternate configurations around the circumference of the head extensions. Such features may take alternate forms, such as wings, flanges, ridges, flexible or retractable pin inserts, and corresponding grooves, notches, bore holes, channels and other features for receiving the engagement features. Thus, the disclosure is intended to be non-limiting and alternate structures known in the art may be used.

Referring now to FIGS. 22-27, a variety of alternate embodiments are depicted, wherein the various features for engagement between the head extensions of the screw subassembly may be adapted for alternate engagement as shown in the depicted embodiments. In the figures, the vertical translation element is shown as elements 1320, 142, 1520, 1620, 1720 and 1820, respectively, each of which engages with its elongate shank shown as 1350, 1450, 1550, 1650, 1750 and 1850, respectively.

In accordance with the various embodiments, the modular anchor assemblies of the invention are advantageous because they provide the surgeon with the option of partially installing an anchor and selecting from modular components to optimize surgical options. The partial installation of the anchor and the ability to select from an array of possible screw heads and rod seats from an array of screw lengths, adjustability and other features provides flexibility that is not possible with conventional systems. In addition, the modular anchor assemblies of the invention are advantageous because they enable vertical adjustability and provide the surgeon with the option of partially locking each screw to the rod. Consequently, prior to completing and finally locking each anchor, the surgeon can readjust the arrangement of the screws and rods to achieve optimal positioning of the anchors, including any vertical adjustment. The partial locked position of the vertically adjustable screw provides flexibility that is not possible with vertically fixed anchors, including flexibility with respect to, compression, distraction, and rotation of the one or more of the components of the fixation system, depending on the number of vertically adjustable anchors that may be used.

In addition to the claims as set forth in this application, this application is directed to a modular spinal fixation assembly, comprising: a bone anchor comprising a modular screw, comprising: a head portion comprising at a proximal end a hemispherical or spherical screw head and an elongate extension situated at a distal end thereof; and a separate threaded shank portion comprising at a distal end a threaded shank and an elongate extension situated at a proximal end thereof, the screw head and threaded shank portions adapted for interconnection along a common elongate axis to form a screw having a spherical head and threaded shank portion and capable of vertical displacement to achieve variable length; the modular screw further comprising a slidable extension disposed at one of the distal end of the screw head and the proximal end of the threaded shank portion, the slidable extension adapted for slidable insertion into a collet; and a collet extension disposed at the other of the distal end of the screw head and the proximal end of the threaded shank portion, wherein the collet extension comprises one or a plurality of vertical slits arranged circumferentially along its elongate axis, each slit extending along at least a portion of the length of the collet extension; and a compression element adapted for direct engagement with one or both of the head and the threaded shank portions of the screw, wherein the compression element is positionable between open and locked arrangements, whereby, when the slidable extension is at least partially inserted into the collet extension and the compression element is actuated from the open arrangement to the locked arrangement, the collet is compressed against the inserted slidable extension to achieve locking there between, and a retaining housing having an upper open receiving end and an opposing base and comprising in the base a bore 33 for receiving the shank of the screw therein and seating the screw head, the retaining housing further comprising a generally U-shaped channel for receiving a surgical rod, the channel accessible from the upper open receiving end and oriented along an axis that is substantially perpendicular to the elongate axis. Further, the above described modular spinal fixation assembly includes a head portion of the screw provided in varying lengths, and wherein either or both the length of the proximal head may be varied and the length of the distal elongate extension may be varied, and wherein the threaded shank portion of the screw is provided in varying lengths, and wherein either or both the length of the distal threaded shank may be varied and the length of the proximal elongate extension may vary; and wherein the head portion of the screw is provided in varying lengths, and wherein either or both the length of the proximal head may be varied and the length of the distal elongate extension may be varied, and, wherein the threaded shank portion of the screw is provided in varying lengths, and wherein either or both the length of the distal threaded shank may be varied and the length of the proximal elongate extension may vary; and wherein the assembly is provided fully assembled; and wherein the assembly further comprises a locking element that is adapted to engage with the retaining housing and a compression washer, and wherein the assembly comprises the compression washer engaged with the head of the screw head portion, the screw head portion is engaged with the threaded shank portion and the screw is engaged with the retaining housing, the compression element is engaged with the collet, and the locking element is reversibly engaged with the retaining housing; and wherein the assembly is provided in a subassembly comprising the screw head portion engaged with the retaining housing, the compression element is engaged with the collet, and wherein the threaded shank portion is provided separately from the screw head portion; and wherein the assembly further comprises a locking element that is adapted to engage with the retaining housing and a compression washer, and wherein the assembly comprises the compression washer engaged with the head of the screw head portion, and the locking element is reversibly engaged with the retaining housing.

In addition, this application is also directed to a surgical method for installing a bone anchor system for spinal fixation, comprising: selecting two or more bone anchor assemblies selected from: conventional bone anchor assemblies comprising a threaded bone screw, a retaining housing having an upper open receiving end and an opposing base and comprising in the base a bore for receiving the shank of the screw therein and seating the screw head, the retaining housing further comprising a generally U-shaped channel for receiving a surgical rod, the channel accessible from the upper open receiving end and oriented along an axis that is substantially perpendicular to the elongate axis, and a locking element for engagement with the retaining housing to lock the surgical rod to the anchor, and a bone anchor as described hereinabove; and selecting a surgical rod; with a suitable driver, driving each of two or more anchors or anchor subassemblies into fixed engagement with corresponding vertebrae, wherein at least one anchor or anchor subassembly includes or is adapted to engage with modular components that allow adjustability, including translation along the vertical axis of the anchor, so as to enable selection of the anchor height by the surgeon; engaging a proximal portion of the modular adjustable anchor, such modular portion selected from a pre-assembled or modular screw head and engagement seat, to provide a means to introduce the surgical rod into engagement with the anchor; optionally incrementally adjusting the height of the anchor so as to achieve engagement of the stabilization element in the anchor; sliding the stabilization element into place within the anchor; introducing a fixation element to at least temporarily fix the stabilization element within the anchor; optionally, adjusting at least the vertical position of the anchor to optimize its height orientation relative to the stabilization element and adjacent anchors; tightening the fixation element to compress the stabilization element within the anchor assembly, thereby fixedly engaging the modular coaxial components of the anchor so as to lock the position of the anchor and also lock its engagement with the surgical rod; wherein each anchor assembly is fully assembled prior to engagement of the threaded bone screw shank with bone; and wherein at least one of the anchor assemblies is provided as a subassembly, wherein either or both the screw head and the retaining housing are provided separately from the threaded shank portion, to effectively enable bottom loading of the retaining housing; and wherein the vertical height of the screw may be varied by selection of the desired length of screw head, or by selection of a standard length and employment of the variable engagement of the collet and slidable extension portions of the threaded shank portion and screw head.

In addition, this application is also directed to a modular bone anchor for securing a bone stabilization element to a bone, the anchor comprising: a modular screw, comprising: a head portion comprising at a proximal end a spherical screw head and an elongate extension situated at a distal end thereof; and a separate threaded shank portion comprising at a distal end a threaded shank portion and an elongate extension situated at a proximal end thereof, the screw head and threaded shank portions adapted for interconnection along a common elongate axis to form a screw having a spherical head and threaded shank portion and capable of vertical displacement to achieve variable length; the modular screw further comprising a slidable extension disposed at one of the distal end of the screw head and the proximal end of the threaded shank portion, the slidable extension adapted for slidable insertion into a collet; and a collet extension disposed at the other of the distal end of the screw head and the proximal end of the threaded shank portion, wherein the collet extension comprises one or a plurality of vertical slits arranged circumferentially along its elongate axis, each slit extending along at least a portion of the length of the collet extension; and a compression element adapted for direct engagement with one or both of the head and the threaded shank portions of the screw, wherein the compression element is positionable between open and locked arrangements, whereby, when the slidable extension is at least partially inserted into the collet extension and the compression element is actuated from the open arrangement to the locked arrangement, the collet is compressed against the inserted slidable extension to achieve locking there between; wherein the head portion of the screw comprises a collet extension at its distal end and the threaded shank portion of the screw comprises a slidable extension at its proximal end, and wherein the compression element comprises a ring adapted for direct engagement with the collet extension, whereby, when the screw portions and the compression element are coaxially assembled, the compression element is seated in an coaxial arrangement around the collet extension of the screw head and is adapted to travel in a vertical dimension between the distal and proximal ends of the collet.

In addition, this application is also directed to a modular bone anchor as described above, wherein the collet comprises, at it distal end, tab head extensions (flanges) that engage a base of the compression element thereby fixing it on the screw head and preventing it from sliding off a distal end of the collet, and wherein the collet comprises a plurality of locking protuberances (flanges, bosses or tabs) arranged between its distal and proximal ends and distributed in a circumferential arrangement around the collet, and wherein, in its open configuration, the compression seat is positioned at the proximal portion of the collet, above the locking protuberances and is retained in this position and restrained from downward vertical travel by the protuberances, thereby allowing the collet to remain in an essentially fully-open configuration permitting free vertical movement of the elongate extension of the threaded shank portion within the collet channel when inserted therein, and wherein locking of the desired vertical position is achieved by sliding the compression element in a distal direction over the locking protuberances to a position between the locking protuberances and the lower flanges, whereby the collet is compressed and/or frictionally locked to the elongate extension of the threaded shank portion; wherein the head portion of the screw is provided in varying lengths, and wherein either or both the length of the proximal head may be varied and the length of the distal elongate extension may be varied; wherein the threaded shank portion of the screw is provided in varying lengths, and wherein either or both the length of the distal threaded shank portion may be varied and the length of the proximal elongate extension may vary; wherein the head portion of the screw is provided in varying lengths, and wherein either or both the length of the proximal head may be varied and the length of the distal elongate extension may be varied, and, wherein the threaded shank portion of the screw is provided in varying lengths, and wherein either or both the length of the distal threaded shank may be varied and the length of the proximal elongate extension may vary.

In addition, this application is also directed to a spinal anchor assembly, comprising: at least one vertically adjustable bone anchor as set forth in any embodiment set forth above and a retaining housing for engaging and securing the bone anchor and a surgical rod; wherein the assembly is provided fully assembled; wherein the assembly further comprises a locking element that is adapted to engage with the retaining housing and a compression washer, and wherein the assembly comprises the compression washer engaged with the head of the screw head portion, the screw head portion is engaged with the threaded shank portion and the screw is engaged with the retaining housing, and the locking element is reversibly engaged with the retaining housing; wherein the assembly is provided in a subassembly comprising the screw head portion engaged with the retaining housing, wherein the threaded shank portion is provided separately; wherein the assembly further comprises a locking element that is adapted to engage with the retaining housing, and a compression washer, and wherein the subassembly comprises the compression washer engaged with the head of the screw head portion, and the locking element is reversibly engaged with the retaining housing.

In addition, this application is also directed to a modular spinal fixation assembly, comprising: a bone anchor comprising a modular screw, comprising: a head portion comprising at a proximal end a hemispherical or spherical screw head and an elongate extension situated at a distal end thereof; and a separate threaded shank portion comprising at a distal end a threaded shank portion and an elongate extension situated at a proximal end thereof, the screw head and threaded shank portions adapted for interconnection along a common elongate axis to form a screw having a spherical head and threaded shank portion and capable of vertical displacement to achieve variable length; the modular screw further comprising a slidable extension disposed at one of the distal ends of the screw head and the proximal end of the threaded shank portion, the slidable extension adapted for slidable insertion into a collet; and a collet extension disposed at the other of the distal end of the screw head and the proximal end of the threaded shank portion, wherein the collet extension comprises one or a plurality of vertical slits arranged circumferentially along its elongate axis, each slit extending along at least a portion of the length of the collet extension; and a compression element adapted for direct engagement with one or both of the head and the threaded shank portions of the screw, wherein the compression element is positionable between open and locked arrangements, whereby, when the slidable extension is at least partially inserted into the collet extension and the compression element is actuated from the open arrangement to the locked arrangement, the collet is compressed against the inserted slidable extension to achieve locking there between, and a retaining housing having an upper open receiving end and an opposing base and comprising in the base a bore 33 for receiving the shank of the screw therein and seating the screw head, the retaining housing further comprising a generally U-shaped channel for receiving a surgical rod, the channel accessible from the upper open receiving end and oriented along an axis that is substantially perpendicular to the elongate axis; wherein the head portion of the screw is provided in varying lengths, and wherein either or both the length of the proximal head may be varied and the length of the distal elongate extension may be varied; wherein the threaded shank portion of the screw is provided in varying lengths, and wherein either or both the length of the distal threaded shank may be varied and the length of the proximal elongate extension may vary; wherein the head portion of the screw is provided in varying lengths, and wherein either or both the length of the proximal head may be varied and the length of the distal elongate extension may be varied, and, wherein the threaded shank portion of the screw is provided in varying lengths, and wherein either or both the length of the distal threaded shank may be varied and the length of the proximal elongate extension may vary; wherein the assembly is provided fully assembled; wherein the assembly further comprises a locking element that is adapted to engage with the retaining housing and a compression washer, and wherein the assembly comprises the compression washer engaged with the head of the screw head portion, the screw head portion is engaged with the threaded shank portion and the screw is engaged with the retaining housing, the compression element is engaged with the collet, and the locking element is reversibly engaged with the retaining housing; wherein the assembly is provided in a subassembly comprising the screw head portion engaged with the retaining housing, the compression element is engaged with the collet, and wherein the threaded shank portion is provided separately from the screw head portion; wherein the assembly further comprises a locking element that is adapted to engage with the retaining housing and a compression washer, and wherein the assembly comprises the compression washer engaged with the head of the screw head portion, and the locking element is reversibly engaged with the retaining housing.

In addition, this application is also directed to a surgical method for installing a bone anchor system for spinal fixation, comprising: selecting two or more bone anchor assemblies selected from: conventional bone anchor assemblies comprising a threaded bone screw, a retaining housing having an upper open receiving end and an opposing base and comprising in the base a bore 33 for receiving the shank of the screw therein and seating the screw head, the retaining housing further comprising a generally U-shaped channel for receiving a surgical rod, the channel accessible from the upper open receiving end and oriented along an axis that is substantially perpendicular to the elongate axis, and a locking element for engagement with the retaining housing to lock the surgical rod to the anchor, and a bone anchor as described above; and selecting a surgical rod; with a suitable driver, driving each of two or more anchors or anchor subassemblies into fixed engagement with corresponding vertebrae, wherein at least one anchor or anchor subassembly includes or is adapted to engage with modular components that allow adjustability, including translation along the vertical axis of the anchor, so as to enable selection of the anchor height by the surgeon; engaging a proximal portion of the modular adjustable anchor, such modular portion selected from a pre-assembled or modular screw head and engagement seat, to provide a means to introduce the surgical rod into engagement with the anchor; optionally incrementally adjusting the height of the anchor so as to achieve engagement of the stabilization element in the anchor; sliding the stabilization element into place within the anchor; introducing a fixation element to at least temporarily fix the stabilization element within the anchor; optionally, adjusting at least the vertical position of the anchor to optimize its height orientation relative to the stabilization element and adjacent anchors; tightening the fixation element to compress the stabilization element within the anchor assembly, thereby fixedly engaging the modular coaxial components of the anchor so as to lock the position of the anchor and also lock its engagement with the surgical rod; wherein each anchor assembly is fully assembled prior to engagement of the threaded bone screw shank with bone; wherein at least one of the anchor assemblies is provided as a subassembly, wherein either or both the screw head and the retaining housing are provided separately from the threaded shank portion, to effectively enable bottom loading of the retaining housing; wherein the vertical height of the screw may be varied by selection of the desired length of the screw head, or by selection of a standard length and employment of the variable engagement of the collet and slidable extension portions of the threaded shank portion and screw head.

In addition, this application is also directed to a vertically adjustable bone anchor for securing a bone stabilization element to a bone, the anchor comprising: a modular screw, comprising: a head portion comprising at a proximal end a spherical screw head and an elongate extension therefrom situated at a distal end thereof, and a separate threaded shank portion comprising at a distal end a threaded shank and an elongate extension therefrom situated at a proximal end thereof, the screw head and threaded shank portions adapted for interconnection along a common elongate axis to form a screw having a hemispherical head and threaded shank and capable of vertical displacement to achieve variable length; and the modular screw further comprising a slidable extension disposed at one of the distal end of the screw head and the proximal end of the threaded shank portion, the slidable extension adapted for slidable insertion into a hollow receiving channel, and a hollow receiving channel extension disposed at the other of the distal end of the screw head and the proximal end of the threaded shank portion adapted to receive all or a portion of the slidable extension; and a collet adapted for positioning along the common elongate axis of the head and threaded shank portions of the screw and comprising one or a plurality of vertical slits arranged along at least a portion of its length along the elongate axis; and a compression element adapted for direct engagement with the assembled screw, wherein the compression element is positionable between open and locked arrangements, and whereby, when the slidable extension, collet and receiving channel are coaxially engaged such that the slidable extension is at least partially inserted into the receiving channel extension, actuation of the compression element from the open arrangement to the locked arrangement compresses the collet against the coaxially arranged head extensions to achieve locking there between, thereby preventing further vertical travel between the screw portions; wherein the collet is an elongate insert that is adapted to receive insertion of the elongate extension and is insertable in the receiving channel extension; wherein the slidable extension comprises a first engagement feature that fixes alignment between the slidable extension, the receiving channel extension and the collet and can be actuated to prevent independent rotation of each of the slidable extensions, the receiving channel extension and the collet around the common elongate axis; wherein the slidable extension comprises a second engagement feature that is independent of the collet, wherein the second engagement feature fixes alignment between the slidable extension and the receiving channel extension and can be actuated to prevent vertical separation (pull out) of the slidable extension and the receiving channel extension; wherein the first engagement feature comprises at least one elongate protuberance oriented along the common elongate axis that terminates at a point above the terminal end of the elongate extension, and wherein the collet comprises a corresponding elongate slot and the receiving channel extension comprises a corresponding elongate channel for receiving the first engagement feature; wherein the second engagement feature comprises at least one projection or boss positioned at the distal end of the slidable extension between the terminal end of the elongate extension and the terminal point of the first engagement feature and is offset from the first engagement feature, and wherein the receiving channel extension comprises a corresponding channel for receiving the second engagement feature that is offset from the channel for receiving the first engagement feature, and wherein the second engagement feature is engagable with the receiving channel extension and is not engagable with the collet, whereby, in use, the slidable extension and collet axially subassembly are aligned and engaged, and wherein upon their initial insertion in the receiving channel extension, the second engagement feature first engages with the corresponding channel of the receiving channel extension, and upon axial rotation thereof the second engagement feature travels within the channel to a point where the first engagement feature is in alignment with its corresponding channel, wherein upon further vertical advancement of the aligned slidable extension and collet within the receiving channel extension, each of the elements of the assembly is restricted from independent rotation around the common elongate axis and the assembly is restricted from vertical disengagement; wherein the head portion of the screw comprises a slidable extension at its distal end and the threaded shank portion of the screw comprises a hollow receiving channel extension at its proximal end, and wherein the collet comprises at its distal end a hemispherical portion that substantially completes a spherical head on the screw head when the two are engaged; wherein the compression element is a spring that that is axially engagable to bias the hemispherical head of the screw head against the hemispherical portion of the collet, wherein in the open arrangement, the screw is no more than partially compressed thereby preventing full insertion of the slidable extension within the collet, and wherein in the closed or locked arrangement, the spring is fully compressed, and the slidable extension is fully inserted within the collet, thereby expanding the collet into compressed and frication engagement within the receiving channel extension.

In addition, this application is also directed to a spinal fixation assembly, comprising: a spinal rod defining a longitudinal axis; at least one vertically adjustable bone anchor as set forth above; a retaining housing for engaging and securing the bone anchor and the surgical rod; a compression washer for engagement between the rod and the bone anchor, and a locking element for securing the rod to the bone anchor; wherein the compression element is actuated by pressure from the spinal fixation assembly locking element, wherein in use, the fixation assembly is assembled, the locking element is engaged in the retaining housing whereby compressive force from the locking element is transmitted to the rod, through the compression washer to the head of the screw thereby transferring compressive force onto the hemispherical head of the screw, thereby compressing the bias spring and urging the hemispherical portions of the screw head and collet together, thereby locking the collet and fixing the vertical position of the anchor.

In addition, this application is also directed to a surgical method for installing a bone anchor system for spinal fixation, comprising: selecting two or more bone anchor assemblies selected from: conventional bone anchor assemblies comprising a threaded bone screw, a retaining housing having an upper open receiving end and an opposing base and comprising in the base a bore 33 for receiving the shank of the screw therein and seating the screw head, the retaining housing further comprising a generally U-shaped channel for receiving a surgical rod, the channel accessible from the upper open receiving end and oriented along an axis that is substantially perpendicular to the elongate axis, and a locking element for engagement with the retaining housing to lock the surgical rod to the anchor, and a bone anchor as set forth above; and selecting a surgical rod; with a suitable driver, driving each of two or more anchors or anchor subassemblies into fixed engagement with corresponding vertebrae, wherein at least one anchor or anchor subassembly includes or is adapted to engage with modular components that allow adjustability, including translation along the vertical axis of the anchor, so as to enable selection of the anchor height by the surgeon; engaging a proximal portion of the modular adjustable anchor, such modular portion selected from a pre-assembled or modular screw head and engagement seat, to provide a means to introduce the surgical rod into engagement with the anchor; optionally incrementally adjusting the height of the anchor so as to achieve engagement of the stabilization element in the anchor; sliding the stabilization element into place within the anchor; introducing a fixation element to at least temporarily fix the stabilization element within the anchor; optionally, adjusting at least the vertical position of the anchor to optimize its height orientation relative to the stabilization element and adjacent anchors; tightening the fixation element to compress the stabilization element within the anchor assembly, thereby fixedly engaging the modular coaxial components of the anchor so as to lock the position of the anchor and also lock its engagement with the surgical rod; wherein each anchor assembly is fully assembled prior to engagement of the threaded bone screw shank with bone; wherein at least one of the anchor assemblies is provided as a subassembly, wherein either or both the screw head and the retaining housing are provided separately from the threaded shank portion, to effectively enable bottom loading of the retaining housing; wherein the vertical height of the screw may be varied by selection of the desired length of screw head, or by selection of a standard length and employment of the variable engagement of the collet and slidable extension portions of the threaded shank portion and screw head.

While various inventive aspects, concepts and features of the general inventive concepts are described and illustrated herein in the context of various exemplary embodiments, these various aspects, concepts and features may be used in many alternative embodiments, and in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, circuits, devices and components, software, hardware, control logic, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A vertically adjustable modular bone anchor comprising: a locking head assembly that includes a proximal head portion comprising an elongate footed collet component and a distal head portion comprising a taper component, each of which collet and taper components comprises at respective distal ends complimentary ramp shaped features, the components being engageable coaxially along a common axis by slidable insertion of one component into a through aperture in the other component along a common axis, and a threaded shank that includes a receiving channel for coaxially receiving the locking head assembly, wherein the modular bone anchor length is varied by sliding the engaged locking head assembly within the shank receiving channel along the common axis, and wherein the modular bone anchor length is selected by compressing together the complimentary ramp shaped features to splay and displace one or both of the distal ends of the collet and taper components away from the common axis and into compressive contact with the receiving channel of the threaded shank.

2. The vertically adjustable modular bone anchor according to claim 1, wherein the taper component is engageable coaxially along a common axis by slidable insertion into a through aperture in the collet component.

3. The vertically adjustable modular bone anchor according to claim 1, wherein the collet component comprises at its distal end a ramp shaped distal foot and the taper component comprises at its distal end a tapered ramp shaped foot that is complimentary to the ramp shaped distal foot of the collet component.

4. The vertically adjustable modular bone anchor according to claim 1, wherein one or both of the elongate footed collet and taper components includes at a proximal end a head that is hemispherical.

5. The vertically adjustable modular bone anchor according to claim 4, wherein one of the elongate footed collet and taper components includes at a proximal end a head that is hemispherical.

6. The vertically adjustable modular bone anchor according to claim 1, wherein one of the elongate footed collet and taper components includes at a proximal end a head that is frusto hemispherical.

7. The vertically adjustable modular bone anchor according to claim 1, wherein the locking head assembly components are engageable from between an open arrangement and a compressed arrangement.

8. The vertically adjustable modular bone anchor according to claim 7, wherein the locking head assembly in the open arrangement provides free movement of the footed collet and taper components along the common axis.

9. The vertically adjustable modular bone anchor according to claim 1, wherein the modular bone anchor is engageable with a retaining housing that is configured for accepting a rod compression screw.

10. A spinal fixation assembly, comprising:
    a vertically adjustable bone anchor for securing a bone stabilization element to a bone comprising:
    a modular screw, comprising:
        a head portion comprising two mating components comprising a proximal head component and a distal head component that are slideably engageable along a common elongate axis, each of the proximal head component and distal head component comprising a proximal end and a distal extension, wherein the distal extensions, when mated, form a substantially cylindrical body;
        a threaded shank portion comprising at a distal end a threaded shank, and at a proximal end a hollow receiving channel for slideably receiving the mated distal extensions of the proximal head component and distal head component;
        the head and threaded shank portions adapted for interconnection along a common elongate axis to form a screw having a substantially spherical head and threaded shank and capable of vertical displacement to achieve variable length; and
        the modular screw further comprising at least one engagement feature that facilitates locking retention of the head portion components with the threaded shank portion when the engagement feature is actuated,
    wherein the proximal and distal head components are positionable between open and compressed arrangements, and whereby, when the mated distal extensions of the proximal head component and distal head component and receiving channel are coaxially engaged such that the mated distal extensions of the proximal head component and distal head component are at least partially inserted in the receiving channel in the open arrangement, the head portion can be vertically adjusted relative to the threaded shank portion, and wherein, when the proximal and distal components of the head portion are actuated into the compressed arrangement the coaxially engaged mated distal extensions of the proximal head component and distal head component and receiving channel are locked, thereby preventing further vertical travel between the head and threaded shank portions.

11. The spinal fixation assembly according to claim 10, wherein the mated distal extensions of the proximal head component and distal head component of the head portion comprises a first engagement feature matable with a corresponding engagement feature within the receiving channel of the threaded shank portion, the engagement of which fixes alignment between one or both proximal and distal head components and the receiving channel to prevent independent rotation of the head portion within the receiving channel around the common elongate axis.

12. The spinal fixation assembly according to claim 10 further comprising:
    a rod defining a longitudinal axis;
    a retaining housing for engaging and securing the vertically adjustable bone anchor and the rod;
    a compression washer for engagement between the rod and the vertically adjustable bone anchor; and
    a locking element for securing the rod to the vertically adjustable bone anchor.

13. The spinal fixation assembly according to claim 12, wherein the compression element is actuated by pressure from the spinal fixation assembly locking element, wherein in use, when the spinal fixation assembly is assembled, the locking element is engaged in the retaining housing whereby compressive force from the locking element is transmitted to the rod, transferring compressive force onto the head portion of the modular screw, thereby locking the vertical position of the vertically adjustable bone anchor.

14. A surgical method for installing a bone anchor system for spinal fixation, comprising:
    selecting:
        a conventional bone anchor assembly comprising a threaded bone screw, a retaining housing having an upper open receiving end and an opposing base and comprising in the base a bore for receiving the and seating the screw, the retaining housing further comprising a generally U-shaped channel for receiving a rod, the channel accessible from the upper open receiving end and oriented along an axis that is substantially perpendicular to the elongate axis, and a locking element for engagement with the retaining housing to lock the surgical rod to the anchor;
        a spinal fixation assembly as claimed in claim 10; and
    a surgical rod;
    affixing the threaded bone screw of the conventional bone anchor assembly into fixed engagement with a first vertebral bone;
    affixing to a second vertebral bone that is adjacent the first vertebral bone the threaded shank portion of the modular screw of the at least one spinal fixation assembly,
    engaging the head portion of the modular screw of the spinal fixation assembly by insertion of mated distal extensions of the proximal head component and distal head component into the receiving channel of the threaded shank portion;
    incrementally adjusting the height of head portion of the modular screw; and
    engaging the surgical rod to lock each of the conventional bone anchor assembly and modular screw into engagement with the first and second vertebral bones.

15. The surgical method according to claim 14, wherein the head and threaded shank portions of the modular screw are assembled prior to engagement of the threaded shank portion with bone, and wherein a retaining housing is provided for one of top and bottom loading of the retaining housing with the threaded shank and head portions of the modular screw.

16. The surgical method according to claim 15, wherein the vertical height of the modular screw may be the same as a standard height of a conventional bone anchor.

\* \* \* \* \*